US012180158B1

(12) United States Patent
Kruegel et al.

(10) Patent No.: US 12,180,158 B1
(45) Date of Patent: Dec. 31, 2024

(54) CRYSTALLINE FUMARATE SALTS OF N-ETHYL-2-(5-FLUORO-1H-INDOL-3-YL)-N-METHYLETHAN-1-AMINE

(71) Applicant: Gilgamesh Pharmaceuticals, Inc., New York, NY (US)

(72) Inventors: Andrew Carry Kruegel, Millington, NJ (US); William Leong, Westfield, NJ (US); Yameng He, Halifax (CA); Lauren MacEachern, Halifax (CA)

(73) Assignee: Gilgamesh Pharmaceuticals, Inc., New York, NY (US)

( * ) Notice: Subject to any disclaimer, the term of this patent is extended or adjusted under 35 U.S.C. 154(b) by 0 days.

(21) Appl. No.: 18/368,124

(22) Filed: Sep. 14, 2023

Related U.S. Application Data

(60) Provisional application No. 63/530,653, filed on Aug. 3, 2023.

(51) Int. Cl.
*C07D 209/16* (2006.01)
(52) U.S. Cl.
CPC ........ *C07D 209/16* (2013.01); *C07B 2200/13* (2013.01)
(58) Field of Classification Search
CPC .................................................. C07D 209/16
See application file for complete search history.

(56) References Cited

U.S. PATENT DOCUMENTS

| 5,846,514 | A | 12/1998 | Foster et al. |
| 8,288,406 | B2 | 10/2012 | Frormann et al. |
| 11,440,879 | B2 | 9/2022 | Kruegel |
| 2012/0095217 | A1 | 4/2012 | Ritter et al. |
| 2012/0122948 | A1 | 5/2012 | Soubhye et al. |
| 2018/0021326 | A1 | 1/2018 | Stamets |
| 2018/0221396 | A1 | 8/2018 | Chadeayne |
| 2020/0030309 | A1 | 1/2020 | Olson |
| 2020/0397752 | A1 | 12/2020 | Perez Castillo et al. |
| 2022/0241243 | A1 | 8/2022 | Kruegel et al. |
| 2023/0293558 | A1 | 9/2023 | Hagel et al. |

FOREIGN PATENT DOCUMENTS

| CA | 1100516 | A | 5/1981 |
| CA | 1105938 | A | 7/1981 |
| CN | 104276993 | A | 1/2015 |
| CN | 110343050 | A | 10/2019 |
| CN | 112174851 | A | 1/2021 |
| CN | 113234036 | A | 8/2021 |
| DE | 1668550 | A1 | 7/1971 |
| DE | 2723937 | A1 | 12/1977 |
| EP | 1956016 | A1 | 8/2008 |
| GB | 853775 | A | 11/1960 |
| KR | 20190120859 | A | 10/2019 |
| WO | 2004000205 | A2 | 12/2003 |
| WO | 2004000845 | A1 | 12/2003 |
| WO | 2004000849 | A2 | 12/2003 |
| WO | 2004043949 | A1 | 5/2004 |
| WO | 2004043967 | A1 | 5/2004 |
| WO | 2005063769 | A1 | 7/2005 |
| WO | 2007017289 | A2 | 2/2007 |
| WO | 2008071455 | A1 | 6/2008 |
| WO | 2010081036 | A2 | 7/2010 |
| WO | 2010136546 | A1 | 12/2010 |
| WO | 2012013343 | A1 | 2/2012 |
| WO | 2018064465 | A1 | 4/2018 |
| WO | 2019077332 | A1 | 4/2019 |
| WO | 2019081764 | A1 | 5/2019 |
| WO | 2019129815 | A1 | 7/2019 |
| WO | 2019160057 | A1 | 8/2019 |
| WO | 2019192602 | A1 | 10/2019 |
| WO | 2019220139 | A1 | 11/2019 |
| WO | 2020120539 | A1 | 6/2020 |
| WO | 2020181194 | A1 | 9/2020 |
| WO | 2020/212948 | A1 | 10/2020 |
| WO | 2021134086 | A1 | 7/2021 |
| WO | 2022008627 | A2 | 1/2022 |
| WO | 2022/047579 | A1 | 3/2022 |
| WO | 2022/256554 | A1 | 12/2022 |
| WO | 2022/272174 | A1 | 12/2022 |
| WO | 2023147424 | A1 | 8/2023 |

OTHER PUBLICATIONS

Abolghasem Moghimi et al., "Synthesis of 2-(2-Fluorophenyl)-2-methylamino-Cyclohexanone as a New Ketamine Derivative", Syn•thetic Communications, vol. 44(14) 2021-2028 (2014). 8 pages.
Brandt Simon D. et al., "Analytical chemistry of synthetic routes to psychoactive tryptamines : Part II. Characterisation of the Speeter and Anthony synthetic route to N,N-dialkylated ttyptamines using GC-E I-IT MS, ES I-TQ-MS-MS and NMR", Analyst, vol. 130(3) 330 (2005). 15 pages.
Adamowicz Piotr et al., "Simple and rapid screening procedure for 143 new psychoactive substances by liquid chromatography•tandem mass spectrometty : Simple and rapid screening procedure for 143 new psychoactive substances", Drng Testing and Analysis, vol. 8 (7) 652-667 (2016). 16 pages.
Valentin Magne et al., "Synthesis of Spiroindolenines via Regioselective Gold (I)-Catalyzed Cyclizations of N-Propargyl T1yptamines", Advanced Synthesis and Catalysis, vol. 359 (22) 4036-4042 (2017). 7 pages.

(Continued)

*Primary Examiner* — Rebecca L Anderson
(74) *Attorney, Agent, or Firm* — Scully, Scott, Murphy & Presser, P.C.

(57) ABSTRACT

The present disclosure relates to a crystalline salt selected from crystalline N-ethyl-2-(5-fluoro-1H-indol-3-yl)-N-methylethan-1-amine fumarate and crystalline N-ethyl-2-(5-fluoro-1H-indol-3-yl)-N-methylethan-1-amine hydrochloride, methods of preparing them, and uses thereof for treating mood disorders. In addition, the present disclosure relates to polymorphs of the aforementioned salts. Further, the present disclosure relates to an oil or amorphous form of N-ethyl-2-(5-fluoro-1H-indol-3-yl)-N-methylethan-1-amine, methods of preparing the same, and uses thereof for treating mood disorders.

30 Claims, 13 Drawing Sheets

(56) References Cited

OTHER PUBLICATIONS

Cozzi, Nicholas V, and Paul F Daley. "Receptor binding profiles and quantitative structure-affinity relationships of some 5-substituted-N,N-diallyltryptamines." Bioorganic & medicinal chemisfly letters vol. 26,3 (2016): 959-964. 6 pages.
Davidsen et al. "Ketamine analogues: Comparative toxicokinetic in vitro -in vivo extrapolation and quantification of 2-fluorodeschloroketamine in forensic blood and hair samples", J. Phann Biomed Anal. l 80: 113049 (2020). 20 pages.
Dinger, Julia et al. "Cytochrome P450 inhibition potential of new psychoactive substances of the tryptamine class." Toxicology Letters vol. 241 (2016): 82-94. 13 pages.
Folprechtova Denisa et al., "Enantioselective potential ofteicoplani--and vancomycin-based superficially porous particles-packed col-mnns for supercritical fluid chromatography", Journal of Chroma-tography A, vol. 1612 (2019). 34 pages.
Folprechtova et al. "Enantioselective potential of teicoplanin- and vancomycin-based superficially porous particles-packed columns for supercritical fluid chromatography" Journal of Chromatography A, 1612, 460687 (2020). 9 pages.
Geoffroy P. et al., "Arynic condensation of ketone enolates 19. Synthesis of polycyclic phenylethanolamines", Tetrahedron Letters, vol. 29(12) 1385-1388(1988). 4 pages.
Han Yixin et al., "Method for the Direct Enantioselective Synthesis of Chiral Primary [alpha]-Amino Ketones by Catalytic α-Amination", Organic Letters, vol. 21(1) 283-286 (2019). 4 pages.
Han, Yixin et al. "Simple Enantioselective Syntheses of (2R,6R)-Hydroxynorketamine and Related Potential Rapid-Onset Antidepressants." Organic letters vol. 19, 19 (2017): 5224-5227. 4 pages.
Hagele et al. "Enantioselective separation of Novel Psychoactive Substances using a Lux® AMP 3µm column and HPLC-UV", Journal of Pharmaceutical and Biomedical Analysis, vol. l 79 (2019). 11 pages.
Kadkhodaei Kian et al., "Separation of enantiomers of new ps--choactive substances by high-performance liquid chromatography", Journal of Separation Science, vol. 41(6) 1274-1286 (2018). 13 pages.
Krotulski et al. "Sample Mining and Data Mining: Combined Real-Time and Retrospective Approaches for the Identification of Emerging Novel Psychoactive Substances", Journal of Forensic Sciences 65(2), 550-562 (2020). 13 pages.
Lednicer D, VonVoigtlander PF, Emmert DE "4-Amino-4-arylcyclohexanones and their derivatives, a novel class of analge-sics. 1. Modification of the aryl ring" J Med Chem vol. 23(4): 424-30 (1980). 7 pages.
Mestria et al. "Method development for the identification of methoxpropamine, 2-fluoro-deschloroketamine and deschloroketamine and their main metabolites in blood and hair and forensic applic--tion", Forensic Sci Int. 323:110817 (2021). 11 pages.
Michely, Julian A et al. "Biotransformation and detectability of the new psychoactive substances N,N-diallyltryptamine (DALT) deriva-tives 5-fluoro-DALT, 7-methyl-DALT, and 5,6-methylenedioxy-DALT in urine using GC-MS, LC-MSn, and LC-HR-MS/MS." Analytical and bioanalytical chemislly vol. 409,6 (2017): 1681-1695. 15 pages.
Michely, Julian A et al. "Dried urine spots—A novel sampling technique for comprehensive LC-MSn drng screening." Analytica chimica acta vol. 982 (2017): 112-121. 10 pages.
Pelchowicz, Z. et al. "N-Alkylated 5-fluorotryptamines." Journal of the Chemical Society (1961 ): 54 | 8-2 1.4 pages.
Pelletier et al. "New psychoactive substance cocktail in an intensive care intoxication case elucidated by molecular networking", Clini-cal Toxicology (2021). 5 pages.
Porpiglia, Nadia et al. "Chiral separation and determination of ketamine and norketamine in hair by capillary electrophoresis." Forensic science international vol. 266 (2016): 304-310. 7 pages.
Ryosuke et al. "Studies on generic analytical conditions of illicit drugs using supercritical fluid chromatography-mass spectrometry", Masashi Kanzei Chuo Bunsekishoho, 58, 45-79 (2019). 35 pages.

Scholten et al. "A machine-assisted approach for the preparation of follow-on pharmaceutical compound libraries" Reaction Chemistry & Engineering vol. 3(2), 210-215 (2018). 6 pages.
Shao et al. "Presence of the ketamine analog of 2-fluorodeschloroketamine residues in wastewater" Drug Test Anal. Sep. 13(9):1650-1657 (2021). 8 pages.
Soubhye, Jalal et al. "Hybrid molecules inhibiting myeloperoxidase activity and serotonin reuptake: a possible new approach of major depressive disorders with inflammatory syndrome." The Journal of pharmacy and pharmacology vol. 66,8 (2014): 1122-32. 11 pages.
Soubhye, Jalal et al. "Structure-based design, synthesis, and pha--macological evaluation of 3-(aminoalkyl)-5-fluoroindoles as myeloperoxidase inhibitors." Journal of medicinal chemislly vol. 53,24 (2010): 8747-59. 13 pages.
Stevens Cal Vin L et al., "Amino Ketone Rearrangements. VI. Synthesis of 2-Alkylamino-2-phenylcyclohexanones 1 a", Journal of Organic Chemistry, vol. 31 (8) 2593-2601 (1996). 10 pages.
Tang et al. "Emergence of new psychoactive substance 2-fluorodeschloroketamine: Toxicology and urinary analysis in a cluster of patients exposed to ketamine and multiple analogues", Forensic Sci Int. 312:110327 (2020). 27 pages.
Wang et al. "Halogen Substitution Influences Ketamine Metabolism by Cytochrome P450 2B6: In Vitro and Computational Approaches", Mol Pharm 16(2):898-906 (2019). 36 pages.
Wang, Shiyu; Li, Changxi "Synthesis of anesthetic compound 2-(o-fluorophenyl)-2-methylaminocyclohexanone hydrochloride (F-ketamine)", Beijing Daxue Xuebao, Ziran Kexueban (2), | 16-19 (1987). 4 pages.
West et al. "Early Warning System for Illicit Drng Use at Large Public Events: Trace Residue Analysis of Discarded Drng Packag-ing Samples", J Am Soc Mass Spectrom. vol 32(10):2604-2614(2021 ). 11 pages.
Yang Xiaoyu et al., "Direct Asymmetric Amination of [alpha]-Branched Cyclic Ketones Catalyzed by a Chiral Phosphoric Acid", Journal of the American Chemical Society, vol. 137(9) 3205-3208 (2015). 4 pages.
Kuhnz et al., "Predicting the Oral Bioavailability of 19-nortestosterone Progestins in vivo from Their Metabolic Stability in Hmnan Liver Microsomal Preparations in vitro", Drug Metabolism and Disposi-tion, vol. 26 (11) 1120-1127 (1998). 8 pages.
Lipton, Stuart A, "Failures and Successes of NMDA Receptor Antagonists: Molecular Basis for the Use of Open-channel Blockers like Memantine in the Treatment of Acute and Chronic Neurologic Insults", NeuroRx, vol. 1(1) 101-110 (2004). 10 pages.
Olivares et al., "N-methyl D-asprutate (NMDA) Receptor Antagonists and Memantine Treatment for Alzheimer's Disease, Vascular Dementia and Parkinson's Disease", Curr Alzheimer Res, vol. 9 (6) 746-758 (2012). 25 pages.
Maurer et al., "Current Use of PSMA-PET in Prostate Cancer Management", Nat Rev Urol., vol. 13 (4) 226-235 (2016). 10 pages.
Obach, Scott R, "Prediction of Human Clearance of Twenty-nine Drugs from Hepatic Microsomal Intrinsic Clearance Data: An Exrunination of in vitro Half-life Approach and Nonspecific Binding to Microsomes", Drug Metab Dispos, vol. 27 (11) 1350-1359 (1999). 10 pages.
Hakkola, J., Hukkanen, J., Turpeinen, M et al. Inhibition and induction of CYP enzymes in humans: an update. Arch Toxicol 94, 3671-3722 (2020). 52 pages.
Setola, V., Roth, B.L. (2006). The Emergence of 5-HT2B Receptors as Targets to Avoid in Designing and Refining Phru-maceuticals. In: Roth, B.L. (eds) The Serotonin Receptors. The Receptors. Humana Press. 20 pages.
Hagele, JS, Hubner, E-M, Schmid, MG. Determination of the chiral status of different novel psychoactive substance classes by capillary electrophoresis and !3-cyclodextrin derivatives. Chirality. 2020; 32 1191-1207. 17 pages.
Kamenka Jean Marc et al., "Recherche de differences conformation-nelles et biochimiques entre phencyclidine et ketamine-[Studies on the conformational and biochemical differences between phen-cyclidine and ketamine]", European Journal of Medicinal Chemis-t.ty, vol. 20(5) 419-424 (1985). 6 pages.
Hashimoto, H., et al., "Actions of D-lysergic acid diethylamide (LSD) and its derivatives on 5-hydroxytryptamine receptors in the

(56) References Cited

OTHER PUBLICATIONS isolated uterine smooth muscle of the rat", European Journal of Pharmacology, Oct. 15, 1977, pp. 341-348, vol. 45, No. 4.

Hoffman, A.J., et al,. "Synthesis and LSD-like discriminative stimulus properties in a series of N(6)-alkyl norlysergic acid N,N-diethylamide derivatives", Journal of Medical Chemistry, Jan. 1, 1985, pp. 1252-1255, vol. 28, No. 9.

Monte, A.P., et al: "Stereoselective LSD-like Activity in a Series of d-Lysergic Acid Amides of (R)- and (S)-2-Aminoalkanes", Journal of Medical Chemistry, Mar. 1, 1995, pp. 958-966, vol. 38, No. 6.

Nichols, D.E., et al, "Lysergamides of Isomeric 2,4-Dimethylazetidines Map the Binding Orientation of the Diethylamide Moiety in the Potent Hallucinogenic Agent N,N-Diethyllysergamide (LSD)", Journal of Medical Chemistry, Sep. 2002, pp. 4344-4349, vol. 45, No. 19.

Rucker, J.J.H., et al., "Psychedelics in the treatment of unipolar mood disorders: a systematic review", Journal of Psychopharmacology, Dec. 1, 2016, pp. 1-10.

Kruegel, A. C., et al., "Crystalline Salts of N-Ethyl-(5-Fluoro-1H-Indol-3-YL)-N-Methylethan-1-Amine", U.S. Appl. No. 18/368,143, filed Sep. 14, 2023, 68 pages.

Kruegel, A. C., et al., "Crystalline Hydrochloride Salts of N-Ethyl-2-(5-Fluoro-1H-Indol-3-YL)-N-Methylethan-1-Amine", U.S. Appl. No. 18/368,099, filed Sep. 14, 2023, 75 pages.

Co-pending U.S. Appl. No. 18/572,861, filed Dec. 21, 2023.
Co-pending U.S. Appl. No. 17/404,923, filed Aug. 17, 2021.
Co-pending U.S. Appl. No. 18/758,102, filed Jun. 28, 2024.
Co-pending U.S. Appl. No. 18/680,473, filed May 31, 2024.

CRYSTALLINE FUMARATE SALTS OF N-ETHYL-2-(5-FLUORO-1H-INDOL-3-YL)-N-METHYLETHAN-1-AMINE

BACKGROUND OF THE DISCLOSURE

Depression is a common psychological problem and refers to a mental state of low mood and aversion to activity. Various symptoms associated with depression include persistent anxious or sad feelings, feelings of helplessness, hopelessness, pessimism, and/or worthlessness, low energy, restlessness, irritability, fatigue, loss of interest in pleasurable activities or hobbies, excessive sleeping, overeating, appetite loss, insomnia, thoughts of suicide, and suicide attempts. The presence, severity, frequency, and duration of the above-mentioned symptoms vary on a case-by-case basis.

Approximately one third of patients with major depressive disorder (MDD) fail to achieve remission of their symptoms, even after multiple rounds of treatment with several known classes of antidepressants, including selective serotonin reuptake inhibitors (SSRIs). This high prevalence of treatment-resistant depression (TRD) makes clear the need for new, more efficacious pharmacotherapies for depression that will target new mechanisms and/or patient populations.

A class of compounds useful for treating depression and mood disorders is described in U.S. Pat. No. 11,440,879, the contents of which are incorporated by reference. It discloses compounds of the formula:

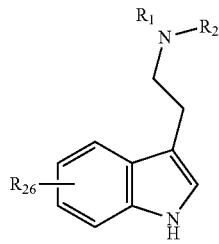

or a pharmaceutically acceptable salt thereof, wherein
$R_1$ is optionally substituted $C_1$-$C_4$ aliphatic;
$R_2$ is optionally substituted $C_1$-$C_4$ aliphatic; and
$R_{26}$ is selected from the group consisting of hydrogen, halogen, —CN, —OH, $C_1$-$C_3$ alkoxy, $C_1$-$C_3$ haloalkyl, OAc, —OPO(OH)$_2$, and NH$_2$.

These compounds are useful for treating mood disorders, including depressive disorders. An example of one such compound within this genus is N-ethyl-2-(5-fluoro-1H-indol-3-yl)-N-methylethan-1-amine. However, to date, N-ethyl-2-(5-fluoro-1H-indol-3-yl)-N-methylethan-1-amine freebase has not been prepared or isolated as a crystalline solid. Although it can be used as an active pharmaceutical ingredient in a pharmaceutical composition, it is preferable to find an active ingredient of this compound that is crystalline for several reasons, including, for example, improved chemical stability, improved ability to remove impurities via recrystallization, improved solubility, improved pharmacokinetic properties, or ease of formulation in pharmaceutical compositions.

Furthermore, many crystalline compounds may exist in more than one crystal form, or polymorph, and relative to one another, these polymorphs exhibit different physical, chemical, and spectroscopic properties. For example, certain polymorphs of a compound may be more chemically stable, may be more readily crystallized, may be more readily soluble in particular solvents, may be more or less hygroscopic, may flow more readily, or may compress more easily than others. See, e.g., "Polymorphism in the Pharmaceutical Industry: Solid Form and Drug Development", Editor(s): Rolf Hilfiker, Markus von Raumer, Wiley-VCH Verlag GmbH & Co. KGaA (2018).

In the case of drugs, certain solid forms may be more bioavailable than others, while others may be more stable under certain manufacturing, storage, and biological conditions. This is particularly important from a regulatory standpoint, since drugs are approved by governmental agencies, such as the U.S. Food and Drug Administration only if they meet exacting purity and characterization standards. Indeed, the regulatory approval of one polymorph of a compound, which exhibits certain solubility and physico-chemical (including spectroscopic) properties, necessarily does not imply the ready approval of other polymorphs of that same compound. Polymorphic forms of a compound are known in the pharmaceutical arts to affect, for example, the solubility, stability, flowability, fractability, and compressibility of the compound, as well as the safety and efficacy of drug products comprising it. See, e.g., Knapman, K. Modern Drug Discoveries, 2000, 53. Therefore, the discovery of new polymorphs of a drug can provide a variety of advantages.

There is a challenge in finding polymorphs of pharmaceuticals. The challenge of finding crystalline polymorphs of a molecule is aided by employing a number of methods known in the art. Such methods include, but are not limited to, melt recrystallization, melt cooling, solvent crystallization, desolvation, rapid evaporation, rapid cooling, slow cooling, vapor diffusion, and sublimation. Polymorphs can be detected, identified, classified, and characterized using well-known techniques such as, but not limited to, differential scanning calorimetry (DSC), thermogravimetry (TGA), X-ray powder diffractometry (XRPD), single crystal X-ray diffractometry, vibrational spectroscopy, solution calorimetry, solid-state nuclear magnetic resonance (NMR), infrared (IR) spectroscopy, Raman spectroscopy, hot-stage optical microscopy, scanning electron microscopy (SEM), electron crystallography and quantitative analysis, particle size analysis (PSA), surface area analysis, solubility, and rate of dissolution. Different physical properties of polymorphs and/or salts can affect their processing. For example, one polymorph or salt might be more likely to form solvates or might be more difficult to filter or wash free of impurities than another due to, for example, the shape or size distribution of particles of it. But, nevertheless, despite these methods, the challenge of finding the proper conditions to finding polymorphs remains huge.

The present inventors have found such crystalline salts and means for preparing and crystallizing the same. This present disclosure encompasses polymorphs of certain salts of N-ethyl-2-(5-fluoro-1H-indol-3-yl)-N-methylethan-1-amine and mixtures of these forms. The present inventors have found crystalline salts of N-ethyl-2-(5-fluoro-1H-indol-3-yl)-N-methylethan-1-amine and the means for preparing the same. Further, as described hereinbelow, it has now been discovered that certain salts of N-ethyl-2-(5-fluoro-1H-indol-3-yl)-N-methylethan-1-amine can be prepared and isolated in a number of crystal forms.

SUMMARY OF THE DISCLOSURE

The present disclosure relates to a crystalline salt selected from crystalline N-ethyl-2-(5-fluoro-1H-indol-3-yl)-N- methylethan-1-amine fumarate and crystalline N-ethyl-2-(5-fluoro-1H-indol-3-yl)-N-methylethan-1-amine hydrochloride, methods of preparing them, and uses thereof for treating mood disorders. In addition, the present disclosure relates to polymorphs of the aforementioned salts. In another embodiment, the present disclosure relates to a solid substantially comprising crystalline N-ethyl-2-(5-fluoro-1H-indol-3-yl)-N-methylethan-1-amine fumarate, crystalline N-ethyl-2-(5-fluoro-1H-indol-3-yl)-N-methylethan-1-amine hydrochloride, or mixtures thereof, methods of preparing them, and uses thereof for treating mood disorders. Further, the present disclosure relates to an oil or amorphous solid form of N-ethyl-2-(5-fluoro-1H-indol-3-yl)-N-methylethan-1-amine, methods of preparing the same, and uses thereof for treating mood disorders.

BRIEF DESCRIPTION OF THE DRAWINGS

The objects, features, and advantages of the present disclosure will become apparent to one of ordinary skill in the art, in view of the following detailed description taken in combination with the attached drawings, in which.

DESCRIPTION OF THE DISCLOSURE

Figure 1:
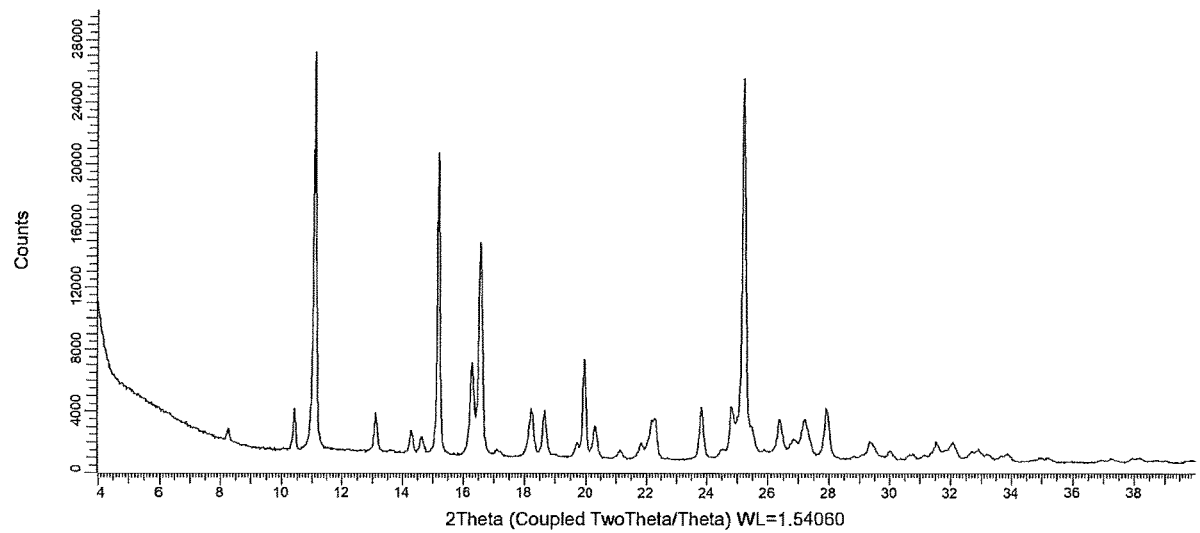
FIG. 1 depicts an XRPD diffractogram of the Form 1 polymorph of N-ethyl-2-(5-fluoro-1H-indol-3-yl)-N-methylethan-1-amine hydrochloride.

The features and other details of the disclosure will now be more particularly described. Before further description of the present disclosure, certain terms employed in the specification, examples, and appended claims are collected here. These definitions should be read in light of the remainder of the disclosure and as understood by a person of ordinary skill in the art. Unless defined otherwise, all technical and scientific terms used herein have the same meaning as commonly understood by a person of ordinary skill in the art.

Unless indicated to the contrary, the term "fumarate salt" or "fumarate", as used herein, is a generic term referring to N-ethyl-2-(5-fluoro-1H-indol-3-yl)-N-methylethan-1-amine fumarates, which include N-ethyl-2-(5-fluoro-1H-indol-3-yl)-N-methylethan-1-amine monofumarate in Form 1; N-ethyl-2-(5-fluoro-1H-indol-3-yl)-N-methylethan-1-amine monofumarate in Form 2; N-ethyl-2-(5-fluoro-1H-indol-3-yl)-N-methylethan-1-amine hemifumarate in Form 1; and N-ethyl-2-(5-fluoro-1H-indol-3-yl)-N-methylethan-1-amine hemifumarate in Form 2. Further, unless indicated to the contrary, as used herein, the term "monofumarate salt", is a subgeneric term that refers to fumarates with a 1:1 base:acid stoichiometry, including N-ethyl-2-(5-fluoro-1H-indol-3-yl)-N-methylethan-1-amine monofumarate in Form 1 and N-ethyl-2-(5-fluoro-1H-indol-3-yl)-N-methylethan-1-amine monofumarate in Form 2. In addition, unless indicated to the contrary, as used herein, the term "hemifumarate salt" is a subgeneric term that refers to fumarates with a 2:1 base:acid stoichiometry, including N-ethyl-2-(5-fluoro-1H-indol-3-yl)-N-methylethan-1-amine hemifumarate in Form 1, and N-ethyl-2-(5-fluoro-1H-indol-3-yl)-N-methylethan-1-amine hemifumarate in Form 2.

In addition, unless indicated to the contrary, as used herein, the term "hydrochloride salt" or "hydrochloride" is a generic term referring to N-ethyl-2-(5-fluoro-1H-indol-3-yl)-N-methylethan-1-amine hydrochloride in Form 1 and N-ethyl-2-(5-fluoro-1H-indol-3-yl)-N-methylethan-1-amine hydrochloride in Form 2; and the metastable Forms 3 and 4 of N-ethyl-2-(5-fluoro-1H-indol-3-yl)-N-methylethan-1-amine hydrochloride.

Unless indicated to the contrary, the term "freebase" or "free base" refers to N-ethyl-2-(5-fluoro-1H-indol-3-yl)-N- methylethan-1-amine in its base, unprotonated form without any counterion, which can be present as an oil or as an amorphous solid.

As used herein, the term "salt", by itself, without any free base name or acid name (such as hydrochloride or fumarate or hemifumarate), unless indicated to the contrary, refers to a crystalline N-ethyl-2-(5-fluoro-1H-indol-3-yl)-N-methylethan-1-amine salt selected from crystalline N-ethyl-2-(5-fluoro-1H-indol-3-yl)-N-methylethan-1-amine hydrochloride, such as, crystalline N-ethyl-2-(5-fluoro-1H-indol-3-yl)-N-methylethan-1-amine hydrochloride Form 1, crystalline N-ethyl-2-(5-fluoro-1H-indol-3-yl)-N-methylethan-1-amine hydrochloride Form 2; crystalline N-ethyl-2-(5-fluoro-1H-indol-3-yl)-N-methylethan-1-amine fumarate, such as, crystalline N-ethyl-2-(5-fluoro-1H-indol-3-yl)-N-methylethan-1-amine monofumarate Form 1, crystalline N-ethyl-2-(5-fluoro-1H-indol-3-yl)-N-methylethan-1-amine monofumarate Form 2, crystalline N-ethyl-2-(5-fluoro-1H-indol-3-yl)-N-methylethan-1-amine hemifumarate Form 1, and crystalline N-ethyl-2-(5-fluoro-1H-indol-3-yl)-N-methylethan-1-amine hemifumarate Form 2.

As defined herein, the term "solvent" refers to a liquid substance or a mixture of liquid substances, which is capable of dissolving another substance (solute) to form a solution, in which the solute is uniformly dispersed at the molecular or ionic size level. For purposes of this disclosure, the solvent may be a reaction solvent or a crystallizing solvent. Solvents referenced herein are inert solvents with respect to the solutes or reactants.

As defined herein, an "inert solvent" is a solvent that does not react with either the reactants or products formed in a chemical reaction.

The term "reaction solvent" or like term is a solvent in which a chemical reaction occurs. It is an inert solvent, i.e., it does not react with either the free base or the acids or the product that is formed. In an embodiment, the free base and the acid are soluble therein, and the product salt may or may not be soluble therein. Further, in an embodiment, it is a volatile solvent.

As used herein, the term "crystallizing solvent" or like term is an inert solvent that is used for the crystallization of a salt of the present disclosure in which the salt is poorly soluble at room temperature or low temperature, but in which it is more soluble when heated, for example, to the boiling point of the solvent. Ideally, the salt is nearly insoluble or sparingly soluble in the solvent at room temperature and extremely soluble at the boiling point of the solvent. The crystallizing solvent may be one solvent or a mixture of solvents. If it is a mixture of liquid solvents, they may be miscible. In an embodiment, water may be a solvent or co-solvent. The term "recrystallizing solvent", as used herein, is a crystallizing solvent, and the two terms may be used interchangeably.

The term "amorphous", as applied to a compound, refers to a state in which the material lacks long-range order at the molecular level, and depending upon temperature, may exhibit the properties of a solid or liquid. Typically, such materials do not give distinctive X-ray diffraction patterns.

The term "crystalline" as applied to a compound refers to a solid phase in which the material has a regular ordered internal structure at the molecular level and gives a distinctive X-ray diffraction pattern with defined peaks.

The term "crystallization", as used throughout this disclosure, can refer to crystallization and/or recrystallization, depending upon the applicable circumstances relating to the preparation of the salts described herein.

As used herein and unless otherwise indicated, the terms "polymorph" and "polymorphic form" refer to solid crystalline forms of a compound or complex. Different polymorphs of the same compound can exhibit different physical, chemical, and/or spectroscopic properties. Different physical properties include, but are not limited to, stability (e.g., to heat or light), compressibility and density (important in formulation and product manufacturing), and dissolution rates (which can affect bioavailability). Differences in stability can result from changes in chemical reactivity (e.g., differential oxidation, such that a dosage form discolors more rapidly when comprised of one polymorph than when comprised of another polymorph) or mechanical characteristics (e.g., tablets crumble on storage as a kinetically favored polymorph converts to a thermodynamically more stable polymorph) or both (e.g., tablets of one polymorph are more susceptible to breakdown at high humidity).

Different physical properties of polymorphs and/or salts can affect their processing. For example, one polymorph might be more likely to form solvates or might be more difficult to filter or wash free of impurities than another due to, for example, the shape or size distribution of particles of it.

Polymorphs of a molecule can be obtained by a number of methods known in the art. Such methods include, but are not limited to, melt recrystallization, melt cooling, solvent crystallization, desolvation, rapid evaporation, rapid cooling, slow cooling, vapor diffusion, and sublimation. Polymorphs can be detected, identified, classified, and characterized using well-known techniques such as, but not limited to, melting point, differential scanning calorimetry (DSC), thermogravimetry (TGA), X-ray powder diffractometry (XRPD), single crystal X-ray diffractometry, vibrational spectroscopy, solution calorimetry, solid state nuclear magnetic resonance (NMR), infrared (IR) spectroscopy, Raman spectroscopy, hot-stage optical microscopy, scanning electron microscopy (SEM), electron crystallography and quantitative analysis, particle size analysis (PSA), surface area analysis, solubility, and rate of dissolution.

When the salts depicted are characterized by or have an XPRD pattern substantially as shown in the aforementioned figures, it is to be understood to mean that the peak pattern is basically as shown with the typical variability in peak position and intensity being taken into account. In an embodiment, at least 70% of the XPRD pattern has the peaks at the values shown with variations at 2θ angles of ±0.50 degrees, and in another embodiment, at least 75% of the XPRD pattern has the peaks at the values shown with variations at 2θ angles of ±0.50, and in another embodiment, at least 80% of the XPRD pattern has the peaks at the values shown with variations at 2θ angles of ±0.50, and in a still further embodiment, at least 85% of the XPRD pattern has the peaks at the values shown with variations at 2θ angles of ±0.50, and in still another embodiment, at least 90% of the XPRD pattern has the peaks at the values shown with variations at 2θ angles of ±0.50. It should be understood, however, that relative intensities and assignment of the peaks of polymorphic forms depicted in these figures can vary depending on a number of factors, including, without limitation, sample preparation, aspect ratio, particle size, mounting, and the instrument and analytical procedure and settings used to obtain the spectrum. As such, the peaks observed in the figures and assignments listed herein in the various tables and figures are intended to encompass variations of ±0.50 degrees 2θ and variations in relative peak intensity understood to be acceptable by one skilled in the art.

As used herein to refer to the spectra or data presented in graphical form (e.g., XRPD, DSC, IR, Raman, and NMR spectra), and unless otherwise indicated, the term "peak" refers to a peak or other special feature that one skilled in the art would recognize as not attributable to background noise.

When listing the peaks for the XRPDs, it is to be understood that each of the values listed are varied by ±0.50° 2θ (or ±0.1, ±0.2, ±0.3 and ±0.4 degrees 2θ), even when ±0.50° 2θ (±0.1, ±0.2, ±0.3 and ±0.4 degrees 2θ). is not recited in the listing. Further, when a listing of the chain of peaks is provided with ±0.50° 2θ at the end of the chain, for purposes of this disclosure, each value in the chain of peaks is modified by the variation ±0.50° 2θ (±0.1, ±0.2, ±0.3 and ±0.4 degrees 2θ).

It should be understood, however, that relative intensities and assignment of the peaks of the salts depicted in these figures can vary depending on a number of factors, including, without limitation, sample preparation, mounting, and the instrument and analytical procedure and settings used to obtain the spectrum. As such, the peaks observed in the figures and assignments listed herein in the various tables and figures are intended to encompass variations of plus or minus 0.5 degrees 2θ. It is to be understood that even though the values of the XRPD peaks may recite a variation of ±0.50° 2θ, this variation also encompasses a variation of the XRPD values of 0.1, ±0.2, ±0.3 and ±0.4 degrees 2θ. Thus, whenever a variation of 0.50° 2θ is listed, it also includes a variation of XRPD values of ±0.1, ±0.2, ±0.3 and ±0.4 degrees 2θ.

In summary, with respect to the term "substantially as shown" regarding XRPD means that variability typical for a particular method is taken into account. For example, with reference to X-ray diffraction peak positions, the term "substantially as shown" refers to that typical variability in peak position and intensity being taken into account. One skilled in the art will appreciate that the peak positions (2θ) will show some variability, typically ±0.5°. But as indicated hereinabove, it also encompasses variability in variation of the XRPD values of 0.1, ±0.2, ±0.3 and ±0.4 degrees 2θ. Thus, the term substantially as shown includes a variation of 0.50° 2θ, and also includes a variation of XRPD values of ±0.1, ±0.2, ±0.3 and ±0.4 degrees 2θ.

With respect to the term substantially as shown with respect to DSC, the variability of values are taken into account. The shape of the thermogram is as shown and but the values of the peaks may vary and the value of the peaks are to be understood to be about the values shown.

As used herein, when reference is made to the spectra or data presented in graphical form (e.g., XRPD, and NMR spectra), and unless otherwise indicated, the term "peak" refers to a peak or other special feature that one skilled in the art would recognize as not attributable to background noise.

As used herein and unless otherwise indicated, the term "substantially pure" when used to describe the freebase, fumarate salt or solid or crystalline material or any other description in relation to the freebase or fumarate salt refers to the solid form of the compound in at least 50% by weight, and in another embodiment, in at least 60% by weight, and in another embodiment, in at least 70% by weight, and in another embodiment, in at least 75% by weight, and in a further embodiment, in at least 80% by weight, and in another embodiment, in at least 90% by weight, and in a further embodiment, in at least 95% by weight, and in an even further embodiment, at least 97%, 98%, 99%, or 100% by weight of the solid. For example, it may be present in 50 wt %, 51 wt %, 52 wt %, 53 wt %, 54 wt %, 55 wt %, 56 wt %, 57 wt %, 58 wt %, 59 wt %, 60 wt %, 61 wt %, 62 wt %, 63 wt %, 64 wt %, 65 wt %, 66 wt %, 67 wt %, 68 wt %, 69 wt %, 70 wt %, 71 wt %, 72 wt %, 73 wt %, 74 wt %, 75 wt %, 76 wt %, 77 wt %, 78 wt %, 79 wt %, 80 wt %, 81 wt %, 82 wt %, 83 wt %, 84 wt %, 85 wt %, 86 wt %, 87 wt %, 88 wt %, 89 wt %, 90 wt %, 91 wt %, 92 wt %, 93 wt %, 94 wt %, 95 wt %, 96 wt %, 97 wt %, 98 wt %, 99 wt %, or 100 wt %, or any value therebetween.

As used herein, the term "substantially pure" as it applies to "N-ethyl-2-(5-fluoro-1H-indol-3-yl)-N-methylethan-1-amine hydrochloride" whenever it appears, whether by itself or with the term "crystalline" or "solid" or "material" refers to N-ethyl-2-(5-fluoro-1H-indol-3-yl)-N-methylethan-1-amine hydrochloride being present in at least 90% by weight, and in a further embodiment, in at least 95% by weight. Thus, it in an even further embodiment, it include that it is present in at least 97%, 98%, 99%, or 100% by weight. For example, the term substantially pure, as it applies to "N-ethyl-2-(5-fluoro-1H-indol-3-yl)-N-methyl-ethan-1-amine hydrochloride" whenever it appears, whether by itself or with the term "crystalline" or "solid" or "material" refers to N-ethyl-2-(5-fluoro-1H-indol-3-yl)-N-methyl-ethan-1-amine hydrochloride being present in 90 wt %, 91 wt %, 92 wt %, 93 wt %, 94 wt %, 95 wt %, 96 wt %, 97 wt %, 98 wt %, 99 wt %, 100 wt % or any value therebetween.

As used herein and unless otherwise indicated, the term "polymorphically pure" when used to describe a polymorph of a compound means a solid form of the compound that comprises that polymorph and is substantially free of other polymorphs of the compound. For example, a representative polymorphically pure polymorph comprises greater than about 80% by weight of one polymorphic form of the compound and less than about 20% by weight of other polymorphic forms of the compound, while in another embodiment, greater than about 90% by weight of one polymorphic form of the compound and less than about 10% by weight of other polymorphic forms of the compound, and in a still further embodiment, greater than about 95% by weight of one polymorphic form of the compound and less than about 5% by weight of other polymorphic forms of the compound, and in an even further embodiment, greater than about 97% by weight of one polymorphic form of the compound and less than about 3% by weight of other polymorphic forms of the compound.

Thus, it includes the polymorph being present in 50 wt %, 51 wt %, 52 wt %, 53 wt %, 54 wt %, 55 wt %, 56 wt %, 57 wt %, 58 wt %, 59 wt %, 60 wt %, 61 wt %, 62 wt %, 63 wt %, 64 wt %, 65 wt %, 66 wt %, 67 wt %, 68 wt %, 69 wt %, 70 wt %, 71 wt %, 72 wt %, 73 wt %, 74 wt %, 75 wt %, 76 wt %, 77 wt %, 78 wt %, 79 wt %, 80 wt %, 81 wt %, 82 wt %, 83 wt %, 84 wt %, 85 wt %, 86 wt %, 87 wt %, 88 wt %, 89 wt %, 90 wt %, 91 wt %, 92 wt %, 93 wt %, 94 wt %, 95 wt %, 96 wt %, 97 wt %, 98 wt %, 99 wt %, or 100 wt %, or any value therebetween.

The term "pharmaceutically acceptable" (such as in the recitation of a pharmaceutically acceptable excipient or carrier) refers to a material that is compatible with administration to a human subject, e.g., the material does not cause an undesirable biological effect. Examples of pharmaceutically acceptable excipients are described in the "Handbook of Pharmaceutical Excipients—Ninth Edition", Edited by Paul J Sheskey, Bruno C Hancock, Gary P Moss, David J Goldfarb (2020).

The terms "treating" and "treatment" refer to ameliorating, suppressing, eradicating, reducing the severity of, decreasing the frequency of, decreasing the incidence of, reducing the risk of, slowing the progression of damage caused by, delaying the onset of the condition, or improving the quality of life of a human patient or subject suffering from a condition.

The terms "about" or "approximately", as used herein, mean within an acceptable error range for the particular value as determined by one of ordinary skill in the art, which will depend in part on how the value is measured or determined, i.e., the limitations of the measurement system. For example, "about" can mean within 3 or more than 3 standard deviations, per the practice in the art. Alternatively, "about" can mean a range of up to 20%, a range of up to 10%, a range of up to 5%, and/or a range of up to 1% of a given value. Alternatively, particularly with respect to biological systems or processes, the term can mean within an order of magnitude, e.g., within 5-fold, or within 2-fold, of a value. "About" and "approximately" are used interchangeably herein.

The terms "effective amount" or "therapeutically effective amount" refer to an amount of a crystalline salt described herein, a pharmaceutical composition comprising the same, a medicament comprising the same, or another material comprising the same, which is effective to achieve a particular pharmacological and/or physiological effect including, but not limited to, reducing the frequency or severity of sadness or lethargy, depressed mood, anxious or sad feelings, diminished interest in all or nearly all activities, significant increased or decreased appetite leading to weight gain or weight loss, insomnia, irritability, fatigue, feelings of worthlessness, feelings of helplessness, inability to concentrate, and recurrent thoughts of death or suicide; or providing a desired pharmacologic and/or physiologic effect, for example, reducing, inhibiting, or reversing one or more of the underlying pathophysiological mechanisms underlying the neurological dysfunction, modulating dopamine levels or signaling, modulating serotonin levels or signaling, modulating norepinephrine levels or signaling, modulating glutamate or GABA levels or signaling, modulating synaptic connectivity or neurogenesis in certain brain regions, or a combination thereof. The precise dosage will vary according to a variety of factors, such as subject-dependent variables (e.g., age, immune system health, clinical symptoms, etc.), the disease or disorder being treated, as well as the route of administration and the pharmacokinetics of the agent being administered.

"Patient" or "subject" refers to animals, and can include any mammal, such as humans, rats, mice, cats, dogs, goats, sheep, horses, monkeys, apes, rabbits, cattle, etc. The mammalian subject can be in any stage of development including adults, children, infants, and neonates.

Unless indicated to the contrary, the terms "drugs" and "medicament" are synonymous.

As used herein, the terms "comprises," "comprising," "includes," "including," "has," "having," or any other variation thereof, are intended to cover a non-exclusive inclusion. For example, a process, method, article, or apparatus that comprises a list of elements is not necessarily limited to only those elements, but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

When referring to a solid, the term "substantially comprising crystalline" followed by reference to a compound name, such N-ethyl-2-(5-fluoro-1H-indol-3-yl)-N-methyl-ethan-1-amine monofumarate Form 1, N-ethyl-2-(5-fluoro-1H-indol-3-yl)-N-methylethan-1-amine monofumarate Form 2, N-ethyl-2-(5-fluoro-1H-indol-3-yl)-N-methyl-ethan-1-amine hemifumarate Form 1, and N-ethyl-2-(5-fluoro-1H-indol-3-yl)-N-methylethan-1-amine hemifumarate Form 2, refers to a solid containing at least 50 wt % of the salt of the specified polymorph in the crystalline state. It may contain other impurities. For example, the compound in an amorphous state may additionally be present, or another polymorph may be present, or other impurities may be present, but the sum of these impurities is not more than 50 wt %. In an embodiment, the solid may contain at least 55 wt % of the salt in a crystalline state, and in another embodiment, at least 60 wt % of the salt in a crystalline state; and in a further embodiment, at least 65 wt % of the salt in a crystalline state; and in a still further embodiment, at least 70 wt % of the salt in a crystalline state, and in a further embodiment, at least 75 wt % of the salt in a crystalline state, and in a further embodiment, at least 80 wt % of the salt in a crystalline state, and in a still further embodiment, at least 85 wt % of the salt in a crystalline state, and in another embodiment, at least 90 wt % of the salt in a crystalline state, and in a still further embodiment, at least 95 wt % of the salt in a crystalline state, and in an even further embodiment, at least 99 wt % of the salt in a crystalline state. Thus the amount of the salt present in the crystalline solid may be 50 wt %, 51 wt %, 52 wt %, 53 wt %, 54 wt %, 55 wt %, 56 wt %, 57 wt %, 58 wt %, 59 wt %, 60 wt %, 61 wt %, 62 wt %, 63 wt %, 64 wt %, 65 wt %, 66 wt %, 67 wt %, 68 wt %, 69 wt %, 70 wt %, 71 wt %, 72 wt %, 73 wt %, 74 wt %, 75 wt %, 76 wt %, 77 wt %, 78 wt %, 79 wt %, 80 wt %, 81 wt %, 82 wt %, 83 wt %, 84 wt %, 85 wt %, 86 wt %, 87 wt %, 88 wt %, 89 wt %, 90 wt %, 91 wt %, 92 wt %, 93 wt %, 94 wt %, 95 wt %, 96 wt %, 97 wt %, 98 wt %, 99 wt %, or 100 wt %, or any value therebetween.

When referring to a solid, the term "substantially comprising crystalline" followed by reference to a compound name, such as N-ethyl-2-(5-fluoro-1H-indol-3-yl)-N-methylethan-1-amine hydrochloride Form 1, N-ethyl-2-(5-fluoro-1H-indol-3-yl)-N-methylethan-1-amine hydrochloride Form 2, refers to a solid containing at least 90 wt % of the salt of the specified polymorph in the crystalline state. It may contain other impurities. For example, the compound in an amorphous state may additionally be present, or another polymorph may be present, or other impurities may be present, but the sum of these impurities is not more than 10 wt %. In an embodiment, the solid may contain at least 92 wt % of the salt in a crystalline state, and in another embodiment, at least 94 wt % of the salt in a crystalline state; and in a further embodiment, at least 95 wt % of the salt in a crystalline state; and in a still further embodiment, at least 97 wt % of the salt in a crystalline state, and in a further embodiment, at least 99 wt % of the salt in a crystalline state. Thus the amount of these salts present in the crystalline solid may be 90 wt %, 91 wt %, 92 wt %, 93 wt %, 94 wt %, 95 wt %, 96 wt %, 97 wt %, 98 wt %, 99 wt %, or 100 wt %, or any value therebetween.

When referring to a solid, the term "substantially comprising freebase" or its chemical name, such as N-ethyl-2-(5-fluoro-1H-indol-3-yl)-N-methylethan-1-amine, refers to a solid containing at least 50 wt % of the freebase. It may contain other impurities. For example, a polymorph may be present, or other impurities may be present, but the sum of these impurities is not more than 50 wt %. In an embodiment, the solid may contain at least 55 wt % of the freebase; and in another embodiment, at least 60 wt % of the freebase; and in a further embodiment, at least 65 wt % of the freebase; and in a still further embodiment, at least 70 wt % of the freebase; and in a further embodiment, at least 75 wt % of the freebase; and in a further embodiment, at least 80 wt % of the freebase, and in a still further embodiment, at least 85 wt % of the freebase; and in another embodiment, at least 90 wt % of the freebase, and in a still further embodiment, at least 95 wt % of the freebase, and in an even further embodiment, at least 99 wt % of the freebase. Thus the amount of the freebase present in the e solid may be 50 wt %, 51 wt %, 52 wt %, 53 wt %, 54 wt %, 55 wt %, 56 wt %, 57 wt %, 58 wt %, 59 wt %, 60 wt %, 61 wt %, 62 wt %, 63 wt %, 64 wt %, 65 wt %, 66 wt %, 67 wt %, 68 wt %, 69 wt %, 70 wt %, 71 wt %, 72 wt %, 73 wt %, 74 wt %, 75 wt %, 76 wt %, 77 wt %, 78 wt %, 79 wt %, 80 wt %, 81 wt %, 82 wt %, 83 wt %, 84 wt %, 85 wt %, 86 wt %, 87 wt %, 88 wt %, 89 wt %, 90 wt %, 91 wt %, 92 wt %, 93 wt %, 94 wt %, 95 wt %, 96 wt %, 97 wt %, 98 wt %, 99 wt %, or 100 wt %, or any value therebetween.

Also, the use of "a" or "an" are employed to describe elements and components described herein. This is done merely for convenience and to give a general sense of the scope of the invention. This description should be read to include one or at least one.

Moreover, the singular also includes the plural and vice versa unless it is obvious that it is meant otherwise.

Further, unless expressly stated to the contrary, "or" refers to an inclusive "or" and not to an exclusive "or." For example, a condition A or B is satisfied by any one of the following: A is true (or present), and B is false (or not present), A is false (or not present), and B is true (or present), and both A and B are true (or present).

Moreover, the term "and/or" is synonymous with the term "or", as used herein.

When a range of values is expressed, an embodiment includes the endpoint of the ranges and all the points therebetween. For example, a range of 6 to 9, includes the value 6 and 9 and all values therebetween. Similarly, when values are expressed as approximations, by use of the antecedent "about," it will be understood that the values range from about the two endpoints, where "about" is defined as herein described. All ranges are inclusive and combinable. Further, reference to values stated in ranges includes each and every value within that range.

Unless otherwise defined, all technical and scientific terms used herein have the same meaning as commonly understood by one of ordinary skill in the art to which this invention belongs. Although methods and materials similar or equivalent to those described herein can be used in the practice or testing of embodiments of the present disclosure, suitable methods and materials are described below. All publications, patent applications, patents, and other references mentioned herein are incorporated by reference in their entirety, unless a particular passage is cited. In case of conflict, the present specification, including definitions, will control. In addition, the materials, methods, and examples are illustrative only and not intended to be limiting.

Unless indicated to the contrary, all percentages are by weight.

The present disclosure relates, in part, to a crystalline salt of N-ethyl-2-(5-fluoro-1H-indol-3-yl)-N-methylethan-1-amine selected from crystalline N-ethyl-2-(5-fluoro-1H-indol-3-yl)-N-methylethan-1-amine hydrochloride and crystalline N-ethyl-2-(5-fluoro-1H-indol-3-yl)-N-methylethan-1-amine fumarate. In an embodiment, the present disclosure relates, in part, to an oil or amorphous solid freebase of N-ethyl-2-(5-fluoro-1H-indol-3-yl)-N-methylethan-1-amine. In an embodiment, the present disclosure relates to crystalline N-ethyl-2-(5-fluoro-1H-indol-3-yl)-N-methylethan-1-amine hydrochloride Form 1, crystalline N-ethyl-2-(5-fluoro-1H-indol-3-yl)-N-methylethan-1-amine hydrochloride Form 2, metastable crystalline N-ethyl-2-(5-fluoro-1H-indol-3-yl)-N-methylethan-1-amine hydrochloride Form 3, metastable crystalline N-ethyl-2-(5-fluoro-1H-indol-3-yl)-N-methylethan-1-amine hydrochloride Form 4, crystalline N-ethyl-2-(5-fluoro-1H-indol-3-yl)-N-methylethan-1-amine monofumarate Form 1, crystalline N-ethyl-2-(5-fluoro-1H-indol-3-yl)-N-methylethan-1-amine monofumarate Form 2, crystalline N-ethyl-2-(5-fluoro-1H-indol-3-yl)-N-methylethan-1-amine hemifumarate Form 1, and crystalline N-ethyl-2-(5-fluoro-1H-indol-3-yl)-N-methylethan-1-amine hemifumarate Form 2, amorphous N-ethyl-2-(5-fluoro-1H-indol-3-yl)-N-methylethan-1-amine freebase, methods of preparing them, and uses thereof for treating mood disorders.

Not all solid pharmaceuticals are crystalline. For example, the free base, N-ethyl-2-(5-fluoro-1H-indol-3-yl)-N-methylethan-1-amine, has not been found to exist as a crystalline solid. Moreover, no one has made heretofore a crystalline salt of N-ethyl-2-(5-fluoro-1H-indol-3-yl)-N-methylethan-1-amine.

The present disclosure not only describes the aforementioned crystalline salts and freebase, but also provides a means for making and using these aforementioned crystalline salts and freebase.

In many cases, the salts of the free base of N-ethyl-2-(5-fluoro-1H-indol-3-yl)-N-methylethan-1-amine are isolated or formed in situ from the reaction of the free base with the appropriate acid. For example, N-ethyl-2-(5-fluoro-1H-indol-3-yl)-N-methylethan-1-amine hydrochloride is prepared from the reaction of the free base and hydrochloric acid; N-ethyl-2-(5-fluoro-1H-indol-3-yl)-N-methylethan-1-amine fumarate is prepared from the reaction of the free base and fumaric acid. Moreover, in many cases, the reaction of the acid with the free base is conducted in a solvent. In an embodiment, the free base is soluble in the solvent, but the product salt is insoluble in the solvent at room temperature. In a further embodiment, the reaction is conducted in a crystallizing solvent.

The present inventors have found that N-ethyl-2-(5-fluoro-1H-indol-3-yl)-N-methylethan-1-amine hydrochloride exits in four polymorphs, which are identified hereinbelow as Form 1, Form 2, Form 3, and Form 4, while N-ethyl-2-(5-fluoro-1H-indol-3-yl)-N-methylethan-1-amine fumarate exists in four distinct forms, two polymorphs of N-ethyl-2-(5-fluoro-1H-indol-3-yl)-N-methylethan-1-amine monofumarate, identified herein as Form 1 and Form 2, and two polymorphs of N-ethyl-2-(5-fluoro-1H-indol-3-yl)-N-methylethan-1-amine hemifumarate, identified herein as Form 1 and Form 2.

In an embodiment, the present disclosure relates to solids which are substantially crystalline forms of N-ethyl-2-(5-fluoro-1H-indol-3-yl)-N-methylethan-1-amine fumarate and N-ethyl-2-(5-fluoro-1H-indol-3-yl)-N-methylethan-1-amine hydrochloride. In other words, the solid comprises a crystalline N-ethyl-2-(5-fluoro-1H-indol-3-yl)-N-methylethan-1-amine salt selected from crystalline N-ethyl-2-(5-fluoro-1H-indol-3-yl)-N-methylethan-1-amine hydrochloride, such as, crystalline N-ethyl-2-(5-fluoro-1H-indol-3-yl)-N-methylethan-1-amine hydrochloride Form 1 or crystalline N-ethyl-2-(5-fluoro-1H-indol-3-yl)-N-methylethan-1-amine hydrochloride Form 2; crystalline N-ethyl-2-(5-fluoro-1H-indol-3-yl)-N-methylethan-1-amine fumarate, such as, crystalline N-ethyl-2-(5-fluoro-1H-indol-3-yl)-N-methylethan-1-amine monofumarate Form 1, crystalline N-ethyl-2-(5-fluoro-1H- indol-3-yl)-N-methylethan-1-amine monofumarate Form 2, crystalline N-ethyl-2-(5-fluoro-1H-indol-3-yl)-N-methylethan-1-amine hemifumarate Form 1, or crystalline N-ethyl-2-(5-fluoro-1H-indol-3-yl)-N-methylethan-1-amine hemifumarate Form 2. The solid may be polymorphically pure, that is, it comprises only one crystalline polymorph described herein, or it may comprise a mixture of two or more of the aforementioned crystalline polymorphs. In an embodiment, the solid contains one polymorph or a mixture of crystalline polymorphs with at least one crystalline polymorph described herein present in at least 50% by weight, and in another embodiment, in at least 70% by weight, and in a further embodiment, at least 75% by weight, and in a further embodiment, at least 80% by weight, and in an even further embodiment, at least 85% by weight, and in an even further embodiment, at least 90% by weight, an in an even further embodiment, at least 95% by weight, and in a further embodiment, in at least 98% by weight, and in a further embodiment, in at least 99% by weight. In another embodiment, the solid comprises a mixture of polymorphs of the same salt, such as more than one crystalline fumarate salt or more than one crystalline hydrochloride salt, but not both a crystalline fumarate salt and a crystalline hydrochloride salt of the present disclosure. For example, the solid may comprise a mixture of the crystalline hydrochloride salt Form 1 and 2. In another embodiment, the solid may contain a mixture of the crystalline fumarate salts and/or hemifumarate salts.

In an embodiment, the solid is polymorphically pure. It contains one crystalline polymorph of the hydrochloride salt such as, for example, hydrochloride Form 1 or hydrochloride Form 2 as the only polymorph described in the disclosure or it may contain one crystalline polymorph of the fumarate salt as described in the disclosure, such as fumarate Form 1 or hemifumarate Form 1, or fumarate form 2 or hemifumarate form 2. However, in another embodiment, it may contain the free base. In addition, regardless of whether the solid is polymorphically pure or contains a mixture, it may contain other materials, such as a pharmaceutically acceptable carrier or adjuvant(s) known in the pharmaceutical arts or optionally non-polymorphic or other impurities.

In an embodiment, the solid may be substantially pure. In another embodiment, it may be polymorphically pure, and in a still further embodiment, it may be both substantially pure and polymorphically pure.

In addition, in an embodiment, the solid is anhydrous, that is, contains less than 5% by weight water, for example 1 wt %, 2 wt %, 3 wt %, 4 wt %, or up to 5 wt %, and any value therebetween. Thus, in an embodiment, the solid is anhydrous and substantially pure, and in another embodiment, is polymorphically pure and is anhydrous, and in a still further embodiment, is substantially pure, polymorphically pure, and is anhydrous.

In another embodiment, the solid may comprise the free base. The free base of N-ethyl-2-(5-fluoro-1H-indol-3-yl)-N-methylethan-1-amine is prepared as described in U.S. Pat. No. 11,440,879, the contents of which are incorporated by reference. Moreover, it can also be prepared from the salt in Example 2 therein or from the salts described in co-pending application entitled "CRYSTALLINE SALTS OF N-ETHYL-(5-FLUORO-1H-INDOL-3-YL)-N-METHYL-ETHAN-1-AMINE" (USSN; 18/368,143), the contents of which are incorporated by reference. The salts are reacted with base, typically in a solvent, by techniques well known in the art. For example, the free base of N-ethyl-2-(5-fluoro-1H-indol-3-yl)-N-methylethan-1-amine is prepared by reacting any of the polymorphs of N-ethyl-2-(5-fluoro-1H-indol-3-yl)-N-methylethan-1-amine hydrochloride or any of the polymorphs of N-ethyl-2-(5-fluoro-1H-indol-3-yl)-N-methylethan-1-amine monofumarate or N-ethyl-2-(5-fluoro-1H-indol-3-yl)-N-methylethan-1-amine hemifumarate with a suitable base, such as $NaHCO_3$, $Na_2CO_3$, NaOH, or KOH, $NH_4OH$, triethylamine, pyridine, and the like. Typically, the basification reaction is conducted in a solvent in which the salt is poorly soluble and the resulting free base product is readily soluble. Typically, this solvent is an organic solvent that is immiscible with water, and the reaction is conducted under basification conditions to effect the formation of the freebase. Following reaction of the salt and base to form the free base of N-ethyl-2-(5-fluoro-1H-indol-3-yl)-N-methylethan-1-amine, the freebase is separated from the reaction mixture. For example, the organic phase is washed with water or an aqueous phase to remove inorganic salts formed in the reaction, residual N-ethyl-2-(5-fluoro-1H-indol-3-yl)-N-methylethan-1-amine salt, or other impurities, while leaving the free base of N-ethyl-2-(5-fluoro-1H-indol-3-yl)-N-methylethan-1-amine in the organic layer. The organic solvent is then evaporated by heating or under reduced pressure to provide the free base of N-ethyl-2-(5-fluoro-1H-indol-3-yl)-N-methylethan-1-amine as an oil or amorphous solid.

EXEMPLIFICATION

The various salts described herein are prepared as described hereinbelow, the techniques of which are known to one of ordinary skill in the art. These examples are illustrative of the techniques for preparing the crystalline N-ethyl-2-(5-fluoro-1H-indol-3-yl)-N-methylethan-1-amine salts. The abbreviations used in the specification are indicated below:
  DSC-Differential Scanning Calorimetry
  NMR-Nuclear Magnetic Resonance
  XRPD-X-ray Powder Diffraction.
  ACN-acetonitrile
  DCM-dichloromethane
  EtOAc-ethyl acetate
  MEK-methyl ethyl ketone
  MtBE-tert-butyl methyl ether
  MIBK-methyl isobutyl ketone
  IPA-isopropyl alcohol
  DW-distilled water
  iPrOAc-isopropyl acetate
  DMSO-dimethyl sulfoxide
  THF-tetrahydrofuran
  TSA-p-toluenesulfonic acid
  Volume-typically 1 ml per gram of compound or 1 microliter per mg of compound In the examples below, various types of data are obtained using various machines. For example, XRPD was performed using a Rigaku MiniFlex 600 in reflection mode (i.e. Bragg-Brentano geometry). Samples were prepared on Si zero-return wafers. The parameters for XRPD methods used are listed below:

| Parameter | Regular scan |
| --- | --- |
| X-ray wavelength | Cu Kα1, 1.540598 Å |
| X-ray tube setting | 40 kV, 15 mA |
| Slit condition | 1.25° div., Ni kβ filter, 0.3 mm rec. |
| Scan mode | Continuous |
| Scan range (°2θ) | 4-30 |
| Step size (°2θ) | 0.05 |

-continued

| Parameter | Regular scan |
|---|---|
| Scan speed (°/min) | 5 |
| Spin | No |

Alternatively, XRPD was performed using a Bruker D8 Advance equipped with LYNXEYE detector in reflection mode (i.e. Bragg-Brentano geometry). Samples were prepared on Si zero-return wafers. The parameters for XRPD methods used are listed below.

| Parameter | Regular scan | High resolution scan |
|---|---|---|
| X-ray wavelength | Cu Kα1, 1.540598 Å | Cu Kα1, 1.540598 Å |
| X-ray tube setting | 40 kV, 40 mA | 40 kV, 40 mA |
| Slit condition | 0.6 mm div. + 2.5° soller | 0.6 mm div. + 2.5° soller |
| Scan mode | Step | Step |
| Scan range (°2θ) | 4-30 | 4-40 |
| Step size (°2θ) | 0.03 | 0.02 |
| Dwell time (s/step) | 0.23 | 0.9 |
| Spin | Yes (0.5 Hz) | Yes (0.5 Hz) |

$^1$H NMR was performed on Bruker Avance 300 MHz or 500 MHz spectrometers. Solids were dissolved in 0.75 mL deuterated solvent in a 4 mL vial, transferred to an NMR tube (Wilmad 5 mm thin wall 8" 200 MHz, 506-PP-8) and analyzed according to the following parameters:

| Parameters - Bruker Avance 300 | |
|---|---|
| Instrument | Bruker Avance 300 MHz spectrometer |
| Temperature | 300 K |
| Probe | 5 mm PABBO BB-1H/DZ-GRD Z104275/0170 |
| Number of scans | 16 |
| Relaxation delay | 1.000 s |
| Pulse width | 14.2500 µs |
| Acquisition time | 2.9999 s |
| Spectrometer frequency | 300.15 MHz |
| Nucleus | $^1$H |

| Parameters - Bruker Avance 500 | |
|---|---|
| Instrument | Bruker Avance 500 MHz spectrometer |
| Temperature | 300 K |
| Probe | 5 mm PABBO BB-1H/D Z-GRD Z113652/0159 |
| Number of scans | 32 |
| Relaxation delay | 1.000 s |
| Pulse width | 14.0000 µs |
| Acquisition time | 3.2506 s |
| Spectrometer frequency | 500.13 MHz |
| Nucleus | $^1$H |

DSC was performed using a TA Discovery DSC. The sample (1-5 mg) was weighed directly in a 40 µL hermetic aluminum pan with a pinhole and analyzed according to the parameters below:

| Parameters | |
|---|---|
| Method | Ramp |
| Sample size | 1-5 mg |
| Heating rate | 10.0° C./min |
| Temperature range | 30 to 300° C. |
| Method gas | $N_2$ at 50.00 mL/min |

I. Polymorphs of N-ethyl-2-(5-fluoro-1H-indol-3-yl)-N-methylethan-1-amine hydrochloride A. N-ethyl-2-(5-fluoro-1H-indol-3-yl)-N-methyl-ethan-1-amine hydrochloride Form 1

Freebase N-ethyl-2-(5-fluoro-1H-indol-3-yl)-N-methyl-ethan-1-amine dissolved in 5 volumes of ethyl acetate solvent was dropwise treated with 0.7 mole equivalent of 1M HCl in ethyl acetate (EtOAc) over a period of 1.5 hours. The mixture was stirred at room temperature until a slightly hazy solution was observed. At this point, an additional 1.3 mole equivalent of 1.0 M HCl in EtOAc solution was added dropwise over 1.5 hours. After HCl addition, the resultant slurry was allowed to stir overnight. The slurry was filtered, washed twice with 2 vol. of EtOAc, and was dried under vacuum at 50° C. overnight. A sample of the dry solid was analyzed by XRPD. The product had the XRPD diffractogram depicted in FIG. 1. The values and intensity of the XPRD peaks are provided below in Table 1.

TABLE 1

XRPD peak table of HCl salt Form 1

| Angle (° 2θ) | d-spacing (Å) | Relative intensity |
|---|---|---|
| 8.26 | 10.69 | 2 |
| 10.42 | 8.48 | 10 |
| 11.10 | 7.96 | 100 |
| 13.11 | 6.75 | 9 |
| 14.30 | 6.19 | 4 |
| 14.64 | 6.05 | 3 |
| 15.18 | 5.83 | 73 |
| 16.28 | 5.44 | 21 |
| 16.56 | 5.35 | 51 |
| 17.10 | 5.18 | 1 |
| 18.23 | 4.86 | 12 |
| 18.66 | 4.75 | 11 |
| 19.72 | 4.50 | 2 |
| 19.94 | 4.45 | 23 |
| 20.32 | 4.37 | 7 |
| 21.14 | 4.20 | 2 |
| 21.83 | 4.07 | 3 |
| 22.28 | 3.99 | 10 |
| 23.82 | 3.73 | 11 |
| 24.54 | 3.62 | 1 |
| 24.81 | 3.59 | 11 |
| 25.20 | 3.53 | 94 |
| 25.44 | 3.50 | 8 |
| 25.89 | 3.44 | 2 |
| 26.37 | 3.38 | 7 |
| 26.84 | 3.32 | 4 |
| 27.20 | 3.28 | 9 |
| 27.91 | 3.19 | 12 |
| 29.33 | 3.04 | 4 |
| 30.01 | 2.98 | 2 |
| 31.53 | 2.84 | 3 |
| 32.08 | 2.79 | 3 |
| 32.71 | 2.74 | 2 |
| 32.92 | 2.72 | 2 |
| 33.87 | 2.64 | 1 |

Note.
Cut-off for relative intensity was 1.

As shown, there are peaks in the X-Ray diffractogram characterized by an X-ray powder diffraction pattern measured using Cu K-alpha radiation comprising peaks at 2θ angles of 11.10±0.50, 15.18±0.50, and 25.20±0.50, with the most intense peak at 11.10±0.50 degrees. In another embodiment, the X-Ray diffractogram is characterized by an X-ray powder diffraction pattern measured using Cu K-alpha radiation comprising peaks at 11.10±0.50, 15.18±0.50, 16.56±0.50, 19.94±0.50, and 25.20±0.50 degrees 2θ. In still another embodiment, the N-ethyl-2-(5-fluoro-1H-indol-3-yl)-N-methylethan-1-amine hydrochloride Form 1 is characterized by an X-ray powder diffraction pattern measured using Cu K-alpha radiation comprising peaks at 11.10±0.50, 15.18 0.50, 16.28±0.50, 16.56±0.50, 18.23±0.50, 18.66±0.50, 19.94±0.50, 23.82±0.50, 25.20±0.50, and 27.91±0.50 degrees 2θ. In still another embodiment, the N-ethyl-2-(5-fluoro-1H-indol-3-yl)-N-methylethan-1-amine hydrochloride Form 1 is characterized by an X-ray powder diffraction pattern measured using Cu K-alpha radiation comprising peaks at 8.26±0.50, 10.42±0.50, 11.10±0.50, 13.11±0.50, 14.30±0.50, 14.64±0.50, 15.18±0.50, 16.28±0.50, 16.56±0.50, 17.10±0.50, 18.23±0.50, 18.66±0.50, 19.72±0.50, 19.94±0.50, 20.32±0.50, 21.14±0.50, 21.83±0.50, 22.28±0.50, 23.82±0.50, 24.54±0.50, 24.81±0.50, 25.20±0.50, 25.44±0.50, 25.89±0.50, 26.37±0.50, 26.84±0.50, 27.20±0.50, 27.91±0.50, 29.33±0.50, 30.01±0.50, 31.53±0.50, 32.08±0.50, 32.71±0.50, 32.92±0.50, and 33.87±0.50 degrees 2θ.

Figure 2:
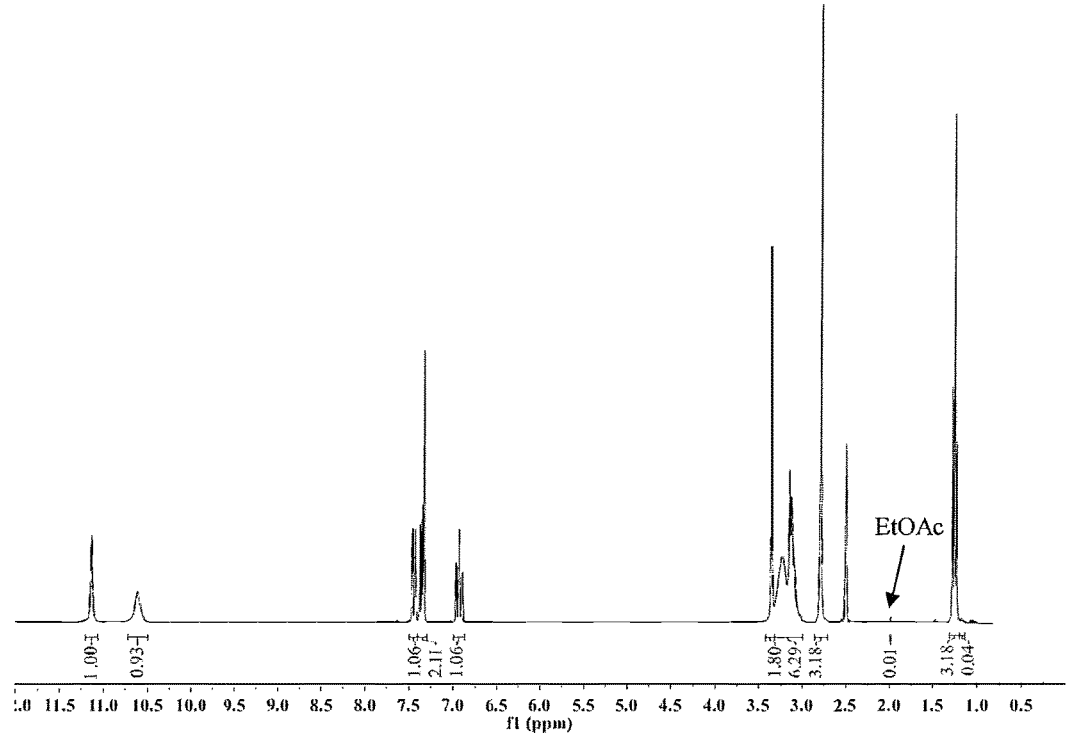
FIG. 2 depicts an $^1$H NMR spectrum (300 MHz, DMSO-$d_6$) of N-ethyl-2-(5-fluoro-1H-indol-3-yl)-N-methylethan-1-amine hydrochloride Form 1.

An $^1$H NMR was also taken of the hydrochloride salt Form 1 and indicates that the salt is comprised of a 1:1 ratio of freebase to acid. The $^1$H NMR spectrum (300 MHz, DMSO-$d_6$) of the hydrochloride salt Form 1 is depicted in FIG. 2.

Figure 3:
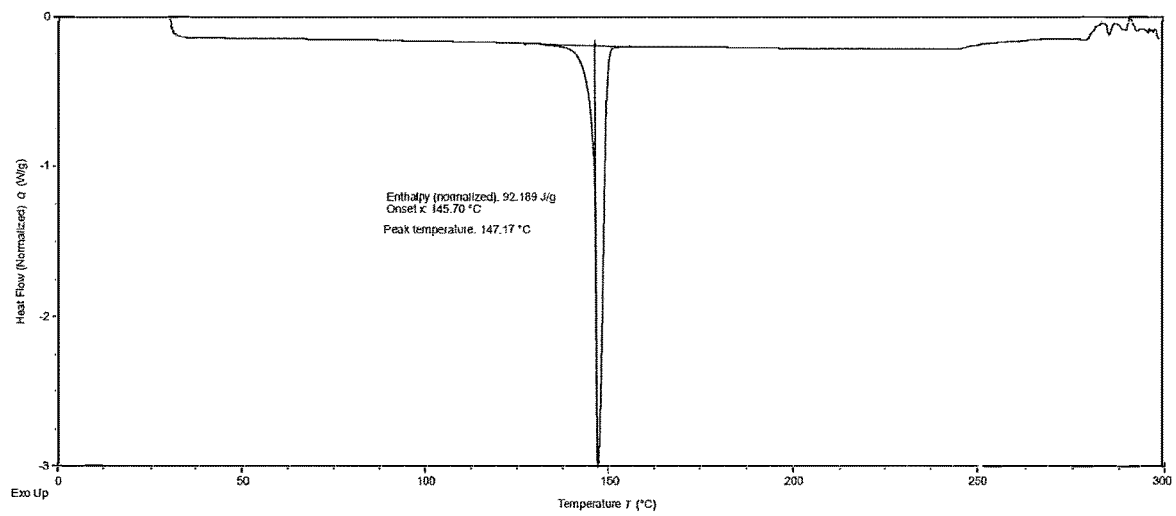
FIG. 3 depicts a DSC thermogram of the Form 1 polymorph of N-ethyl-2-(5-fluoro-1H-indol-3-yl)-N-methylethan-1-amine hydrochloride.

The DSC thermogram of the hydrochloride salt Form 1 was recorded with the same parameters as described above and is depicted in FIG. 3. A sharp peak temperature at about 147° C. was observed.

The morphology of the hydrochloride salt Form 1 was fine particles.

B. Screening and Identification of Additional Forms of N-ethyl-2-(5-fluoro-1H-indol-3-yl)-N-methylethan-1-amine hydrochloride Additional polymorphic forms of the hydrochloride salt were discovered in screening studies, tabulated in Table 2, using N-ethyl-2-(5-fluoro-1H-indol-3-yl)-N-methylethan-1-amine hydrochloride Form 1 as the input material in short-term slurry experiments and crystallization experiments using a slow cooling rate. In total, including the N-ethyl-2-(5-fluoro-1H-indol-3-yl)-N-methylethan-1-amine hydrochloride Form 1, the experiments uncovered 4 polymorphic forms: the aforementioned Form 1, a new polymorphic Form 2, and two meta-stable forms, Forms 3 and 4. In each of the short-term slurry experiments, a quantity of N-ethyl-2-(5-fluoro-1H-indol-3-yl)-N-methylethan-1-amine hydrochloride Form 1 was added to a small quantity of a solvent (quantity selected so that some solids remained undissolved) and the resulting slurry was mixed and allowed to stand for 2 days. At this time, the solids were collected by filtration and analyzed by XRPD, both as the wet cake and after drying under vacuum. The results from these short-term slurry experiments are summarized in Table 2.

TABLE 2

Summary of XRPD patterns of solids obtained from short-term slurry experiments beginning with N-ethyl-2-(5-fluoro-1H-indol-3-yl)-N-methylethan-1-amine hydrochloride

| | XRPD pattern | | | |
| --- | --- | --- | --- | --- |
| | RT | | 50° C. | |
| Solvent | Recovered wet cake | Cake after drying | Recovered wet cake | Cake after drying |
| EtOAc | Form 1 | Form 1 | Form 1 + 2 | — |
| IPA | Form 2 | — | — | — |
| Acetone | Form 2 | — | Form 2 | — |
| ACN | Form 2 | Form 2 | Form 2 | — |
| THF | Form 2 with some form 3 characteristics | — | Form 2 with some form 3 characteristics | — |
| Toluene | Form 1 | — | Form 1 | — |
| DCM | Form 2 | — | — | — |
| 1,4-Dioxane | Form 1 + trace of 2 | Form 1 + trace of 2 | Form 1 + 2 | — |
| Heptane | Form 1 | — | Form 1 | — |
| MtBE | Form 1 | — | Form 1 | — |
| MIBK | Form 1 + 2 | Form 1 + 2 | Form 1 + 2 | Form 1 + 2 |

Note.
Hyphen indicates that no data was collected.

The metastable Forms 3 and 4 of N-ethyl-2-(5-fluoro-1H-indol-3-yl)-N-methylethan-1-amine hydrochloride were discovered using slow crystallization techniques starting with N-ethyl-2-(5-fluoro-1H-indol-3-yl)-N-methylethan-1-amine hydrochloride Form 1. In each of the slow crystallization experiments, a small quantity of N-ethyl-2-(5-fluoro-1H-indol-3-yl)-N-methylethan-1-amine hydrochloride Form 1 was dissolved in the indicated amount of a solvent at 50° C. The resulting solution was then cooled at a rate of 5° C. per hour from 50° C. to 5° C. and the resulting solids were collected by filtration and analyzed by XRPD, both as the wet cake and after drying under vacuum. The results from the slow crystallization experiments are summarized in Table 3.

TABLE 3

Summary of XRPD patterns of solids obtained from slow-cooling crystallization.

| | | XRPD pattern | |
| --- | --- | --- | --- |
| Solvent | Volumes of solvent | Recovered wet cake | Cake after drying |
| EtOH | 2 | Form 4 | — |
| IPA | 15 | Form 3 | — |
| Acetone | 55 | Form 3 + trace of Form 1 | Form 4 + trace of Form 1 |
| ACN | 17 | Form 2 | — |
| ACN:water (95:5 vol.) | 2 | Form 3 | — |
| Acetone: water (97:3 vol.) | 4 | Form 3 | — |

Note.
Hyphen indicates no data were collected.

C. N-ethyl-2-(5-fluoro-1H-indol-3-yl)-N-methylethan-1-amine hydrochloride Form 2

The following procedure was used to generate additional N-ethyl-2-(5-fluoro-1H-indol-3-yl)-N-methylethan-1-amine hydrochloride Form 2.

N-ethyl-2-(5-fluoro-1H-indol-3-yl)-N-methylethan-1-amine hydrochloride Form 1 was dissolved in 10 volumes of ACN. The mixture was stirred at room temperature for 20 min. The white slurry was seeded with a micro-spatula tip of HCl Form 2, which was isolated from the slow cooling crystallization experiments described above. The solids were filtered after stirring at room temperature for 4 days and were washed with ACN. The wet cake was sampled for XRPD. The solid was then dried overnight under vacuum. The dry solid was N-ethyl-2-(5-fluoro-1H-indol-3-yl)-N-methylethan-1-amine hydrochloride Form 2 in crystalline form, as confirmed by XRPD. Its morphology was irregular crystals.

Figure 4:
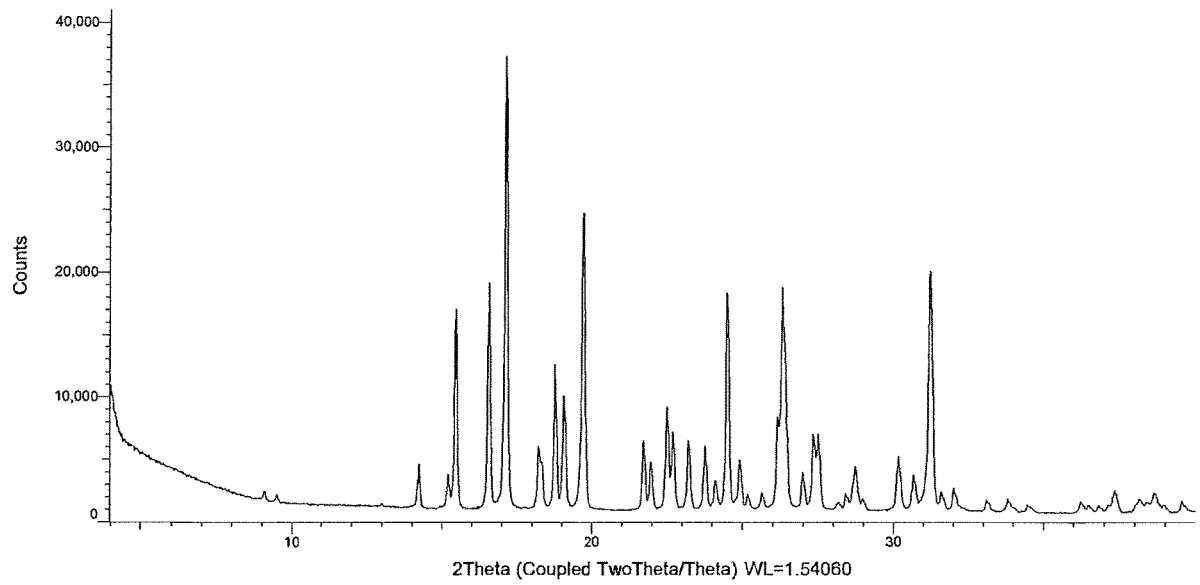
FIG. 4 depicts an XRPD diffractogram of the Form 2 polymorph of N-ethyl-2-(5-fluoro-1H-indol-3-yl)-N-methylethan-1-amine hydrochloride.

The XRPD diffractogram of N-ethyl-2-(5-fluoro-1H-indol-3-yl)-N-methylethan-1-amine hydrochloride Form 2 is depicted in FIG. 4. The values and intensity of the XPRD peaks are provided below in Table 4.

TABLE 4

XPRD peak table of HCl salt Form 2

| Angle (° 2θ) | d-spacing (Å) | Relative intensity |
| --- | --- | --- |
| 9.09 | 9.72 | 1 |
| 9.50 | 9.30 | 1 |
| 14.22 | 6.22 | 7 |
| 15.21 | 5.82 | 8 |
| 15.47 | 5.72 | 43 |
| 16.57 | 5.34 | 50 |
| 17.12 | 5.17 | 100 |
| 18.21 | 4.87 | 11 |
| 18.31 | 4.84 | 11 |
| 18.76 | 4.73 | 32 |
| 19.06 | 4.65 | 26 |
| 19.70 | 4.50 | 67 |
| 21.71 | 4.09 | 13 |
| 21.96 | 4.04 | 10 |
| 22.50 | 3.95 | 23 |
| 22.69 | 3.92 | 17 |
| 23.21 | 3.83 | 14 |
| 23.76 | 3.74 | 12 |
| 24.11 | 3.69 | 5 |
| 24.48 | 3.63 | 43 |
| 24.91 | 3.57 | 9 |
| 25.18 | 3.53 | 3 |
| 25.65 | 3.47 | 3 |
| 26.16 | 3.40 | 20 |
| 26.31 | 3.39 | 49 |
| 26.99 | 3.30 | 7 |
| 27.34 | 3.26 | 15 |
| 27.50 | 3.24 | 14 |
| 28.19 | 3.16 | 1 |
| 28.41 | 3.14 | 3 |
| 28.73 | 3.11 | 9 |
| 28.95 | 3.08 | 2 |
| 30.16 | 2.96 | 9 |
| 30.67 | 2.91 | 7 |
| 31.21 | 2.86 | 53 |
| 31.60 | 2.83 | 4 |
| 32.02 | 2.79 | 5 |
| 33.11 | 2.70 | 2 |
| 34.46 | 2.60 | 2 |
| 36.24 | 2.38 | 2 |
| 36.49 | 2.46 | 2 |
| 36.85 | 2.44 | 1 |
| 37.13 | 2.42 | 2 |
| 37.36 | 2.41 | 4 |
| 38.16 | 2.36 | 2 |
| 38.40 | 2.34 | 2 |
| 38.65 | 2.33 | 4 |
| 38.94 | 2.31 | 1 |
| 39.57 | 2.28 | 2 |

As shown, the N-ethyl-2-(5-fluoro-1H-indol-3-yl)-N-methylethan-1-amine hydrochloride Form 2 is characterized by an X-ray powder diffraction pattern measured using Cu K-alpha radiation comprising peaks at 17.12±0.50° 2θ, 19.70±0.50° 2θ, and 31.21±0.20° 2θ, with the most intense peak at 17.12±0.50° 2θ. In another embodiment, the N-ethyl-2-(5-fluoro-1H-indol-3-yl)-N-methylethan-1-amine hydrochloride Form 2 is characterized by an X-ray powder diffraction pattern measured using Cu K-alpha radiation comprising peaks at 16.57±0.50, 17.12±0.50, 19.70±0.50, 26.31±0.50, and 31.21±0.50 degrees 2θ. In a further embodiment, the N-ethyl-2-(5-fluoro-1H-indol-3-yl)-N-methylethan-1-amine hydrochloride Form 2 is characterized by an X-ray powder diffraction pattern measured using Cu K-alpha radiation comprising peaks at 15.47±0.50, 16.57±0.50, 17.12±0.50, 18.76±0.50, 19.06±0.50, 19.70±0.50, 22.50±0.50, 24.48±0.50, 26.31±0.50, and 31.21±0.50 degrees 2θ. In a still further embodiment, the N-ethyl-2-(5-fluoro-1H-indol-3-yl)-N-methylethan-1-amine hydrochloride Form 2 is characterized by an X-ray powder diffraction pattern measured using Cu K-alpha radiation comprising peaks at 9.09±0.50, 9.50±0.50, 14.22±0.50, 15.21±0.50, 15.47±0.50, 16.57±0.50, 17.12±0.50, 18.21±0.50, 18.31±0.50, 18.76±0.50, 19.06±0.50, 19.70±0.50, 21.71±0.50, 21.96±0.50, 22.50±0.50, 22.69±0.50, 23.21±0.50, 23.76±0.50, 24.11±0.50, 24.48±0.50, 24.91±0.50, 25.18±0.50, 25.65±0.50, 26.16±0.50, 26.31±0.50, 26.99±0.50, 27.34±0.50, 27.50±0.50, 28.19±0.50, 28.41±0.50, 28.73±0.50, 28.95±0.50, 30.16±0.50, 30.67±0.50, 31.21±0.50, 31.60±0.50, 32.02±0.50, 33.11±0.50, 33.81±0.50, 34.46±0.50, 36.24±0.50, 36.49±0.50, 36.85±0.50, 37.13±0.50, 37.36±0.50, 38.16±0.50, 38.40±0.50, 38.65±0.50, 38.94±0.50, and 39.57±0.50 degrees 2θ.

Figure 5:
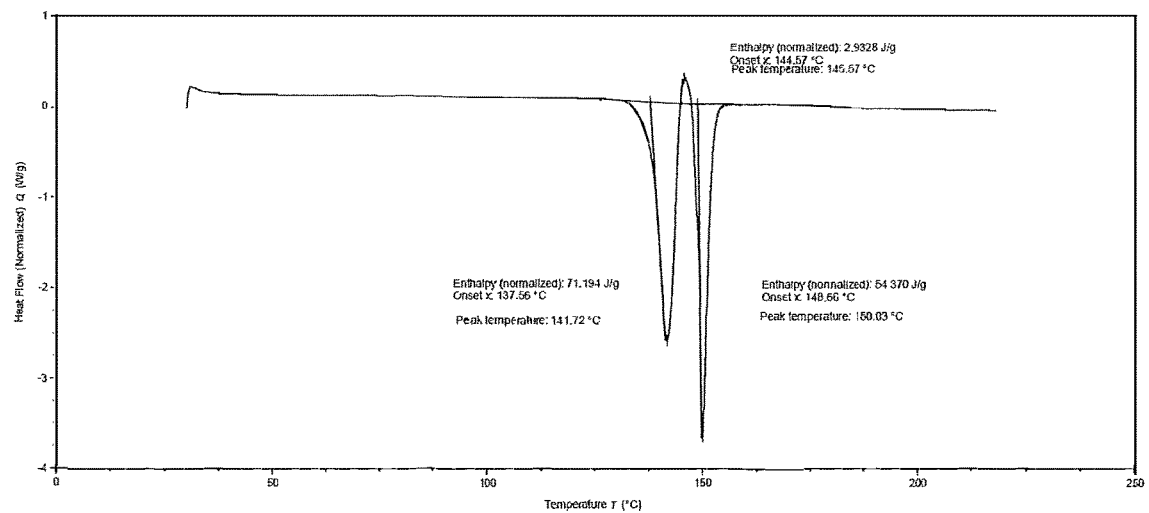
FIG. 5 depicts a DSC thermogram of the Form 2 polymorph of N-ethyl-2-(5-fluoro-1H-indol-3-yl)-N-methylethan-1-amine hydrochloride.

The DSC thermogram of this product was collected with the same parameters as described above, and the DSC thermogram of the hydrochloride salt Form 2 is depicted in FIG. 5. As seen in FIG. 5, there are three temperature peaks: a first minimum temperature peak at about 142° C., one maximum temperature peak at about 146° C., and a second minimum temperature peak at about 150° C.

D. N-ethyl-2-(5-fluoro-1H-indol-3-yl)-N-methylethan-1-amine hydrochloride Metastable Forms 3 and 4

There are two meta-stable N-ethyl-2-(5-fluoro-1H-indol-3-yl)-N-methylethan-1-amine hydrochlorides discussed above, which are identified as Form 3 and Form 4.

Metastable Form 3 was also generated via reactive crystallization by treating N-ethyl-2-(5-fluoro-1H-indol-3-yl)-N-methylethan-1-amine freebase oil with 0.4 mole equivalent of 1M HCl in ethyl acetate (EtOAc) added dropwise over 30 minutes. The mixture was seeded with Form 3 crystals (generated previously from the slow cooling crystallization experiments) and stirred for 30 min. Another 0.7 mole equivalent of 1.0 M HCl in EtOAc solution was then added dropwise over 1 h. After this second HCl addition, a beige slurry was obtained. The slurry was allowed to stir overnight. The slurry was filtered and the filter cake was washed twice with 2 vol. of EtOAc. The recovered solid was dried under vacuum at 50° C. overnight. A sample of the dry solid was analyzed by XRPD, and the pattern was consistent with that of N-ethyl-2-(5-fluoro-1H-indol-3-yl)-N-methylethan-1-amine hydrochloride metastable Form 3.

Figure 6:
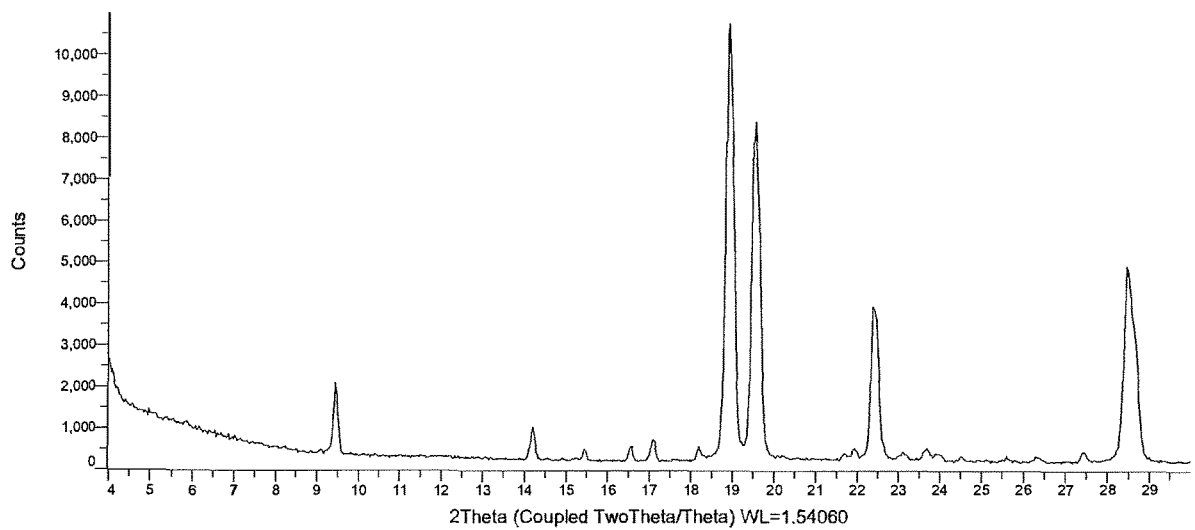
FIG. 6 depicts an XRPD diffractogram of a first metastable polymorph of N-ethyl-2-(5-fluoro-1H-indol-3-yl)-N-methylethan-1-amine hydrochloride identified herein as Form 3.

The XRPD diffractogram of Form 3 is depicted in FIG. 6; the values and relative intensity of the peaks are provided in Table 5 below.

TABLE 5

XRPD peak table of HCl salt metastable Form 3

| Angle (° 2θ) | d-spacing (Å) | Relative intensity |
|---|---|---|
| 9.44 | 9.36 | 15 |
| 14.19 | 6.23 | 5 |
| 15.45 | 5.73 | 2 |
| 16.57 | 5.35 | 2 |
| 17.09 | 5.18 | 3 |
| 18.19 | 4.87 | 2 |
| 18.89 | 4.70 | 100 |
| 19.52 | 4.54 | 75 |
| 21.69 | 4.09 | 1 |
| 21.93 | 4.05 | 2 |
| 22.37 | 3.97 | 34 |
| 23.11 | 3.85 | 1 |
| 23.69 | 3.75 | 2 |
| 23.91 | 3.72 | 1 |
| 24.52 | 3.63 | 1 |
| 25.61 | 3.48 | 1 |
| 26.30 | 3.39 | 1 |
| 27.43 | 3.25 | 2 |
| 28.45 | 3.13 | 42 |

Note.
Cut-off for relative intensity was 1.

Figure 7:
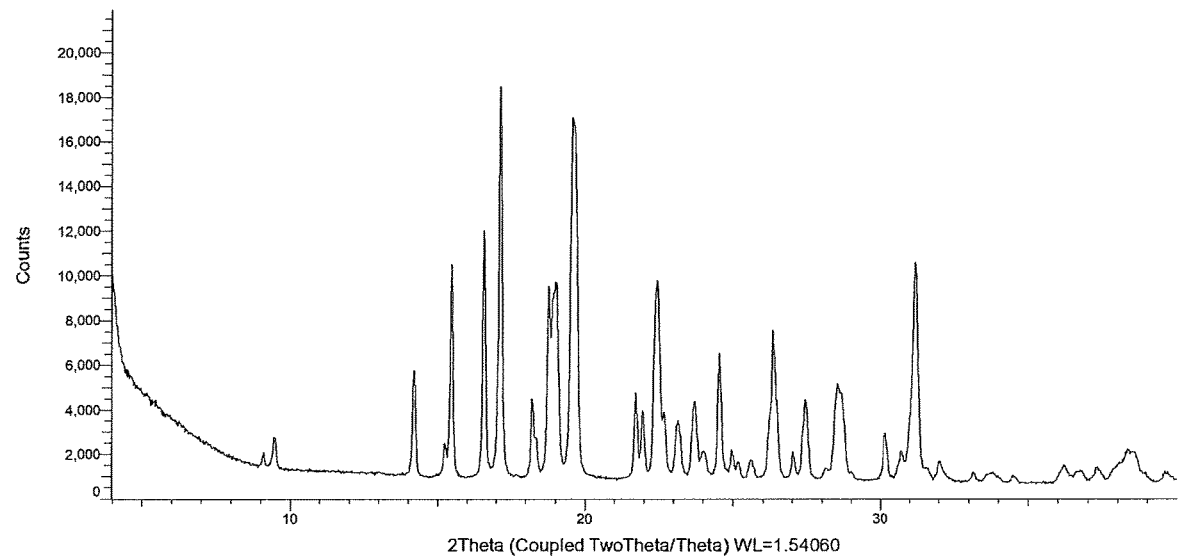
FIG. 7 depicts an XRPD diffractogram of a second metastable polymorph of N-ethyl-2-(5-fluoro-1H-indol-3-yl)-N-methylethan-1-amine hydrochloride, identified herein as Form 4.

The XRPD diffractogram of metastable Form 4 is depicted in FIG. 7; the values and relative intensity of the peaks are provided in Table 6 below. Form 4 samples are prepared from slow cooling crystallization using ethanol solvent as described in Table 3.

TABLE 6

XRPD peak table of HCl salt metastable Form 4.

| Angle (° 2θ) | d-spacing (Å) | Relative intensity |
|---|---|---|
| 9.10 | 9.71 | 3 |
| 9.45 | 9.36 | 7 |
| 14.20 | 6.23 | 26 |
| 15.24 | 5.81 | 6 |
| 15.47 | 5.72 | 53 |
| 16.58 | 5.34 | 63 |
| 17.12 | 5.18 | 100 |
| 18.21 | 4.87 | 15 |
| 18.34 | 4.83 | 7 |
| 18.77 | 4.72 | 48 |
| 19.00 | 4.67 | 50 |
| 19.57 | 4.53 | 94 |
| 21.72 | 4.09 | 21 |
| 21.95 | 4.05 | 17 |
| 22.44 | 3.96 | 51 |
| 22.67 | 3.92 | 16 |
| 23.15 | 3.84 | 14 |
| 23.72 | 3.75 | 18 |
| 24.02 | 3.70 | 5 |
| 24.54 | 3.62 | 32 |
| 24.96 | 3.56 | 6 |
| 25.17 | 3.54 | 3 |
| 25.60 | 3.48 | 3 |
| 26.34 | 3.38 | 38 |
| 27.03 | 3.30 | 6 |
| 27.45 | 3.25 | 20 |
| 28.12 | 3.17 | 2 |
| 28.52 | 3.13 | 24 |
| 28.64 | 3.11 | 22 |
| 28.99 | 3.08 | 2 |
| 30.15 | 2.96 | 10 |
| 30.70 | 2.91 | 6 |
| 31.18 | 2.87 | 57 |
| 31.54 | 2.83 | 2 |
| 32.00 | 2.79 | 4 |
| 33.14 | 2.70 | 2 |
| 33.81 | 2.65 | 2 |
| 34.49 | 2.60 | 2 |
| 36.21 | 2.48 | 3 |
| 36.63 | 2.45 | 2 |
| 36.77 | 2.44 | 2 |
| 37.31 | 2.41 | 3 |
| 37.85 | 2.37 | 3 |
| 38.36 | 2.34 | 8 |
| 38.53 | 2.33 | 8 |
| 38.93 | 2.31 | 2 |
| 39.65 | 2.27 | 1 |

Note.
Cut-off for relative intensity was 1.

II. Polymorphs of N-ethyl-2-(5-fluoro-1H-indol-3yl)-N-methylethan-1-amine Fumarate A. Screening and Identification of Polymorphs of N-ethyl-2-(5-fluoro-1H-indolyl-3-yl)-N-methylethan-1-amine monofumarate The two different polymorphic forms of N-ethyl-2-(5-fluoro-1H-indol-3-yl)-N-methylethan-1-amine monofumarate were discovered by reactive crystallization from various solvents. These crystallization experiments were performed by subjecting the in-situ created salt, made by evaporating an ethanol solution of free base and fumaric acid, to vigorous agitation in 10 volumes of the selected solvent. The agitated mixtures were heated to 45-50° C. and cooled to room temperature as necessary to induce crystallization. Form 1 was the predominant form from acetone, and the mixed ethanol/MTBE solvent system, whereas, Form 2 was produced from IPA solvent (see Table 7 below). It is noted that N-ethyl-2-(5-fluoro-1H-indol-3-yl)-N-methylethan-1-amine monofumarate Form 2 solids that were exposed to humidity (90% RH/30° C.) slowly converted to Form 1.

TABLE 7

Polymorphs of N-ethyl-2-(5-fluoro-1H-indol-3-yl)-N-methylethan-1-amine monofumarate formed by reactive crystallization from different solvents.

| | | XRPD pattern | | |
|---|---|---|---|---|
| Counter-ion | Solvent | Isolated Wet cake | Cake after drying | Dry cake exposed to humidity |
| Fumaric acid (1.1 eq.) | EtOH:MTBE (1:1 vol.) | Form 1 | — | — |
| | Acetone | Form 1 | Form 1 | Form 1 |
| | IPA | Form 2 | Form 2 | Form 1 |

B. N-ethyl-2-(5-fluoro-1H-indolyl-3-yl)-N-methylethan-1-amine Monofumarate Form 1

Figure 8:
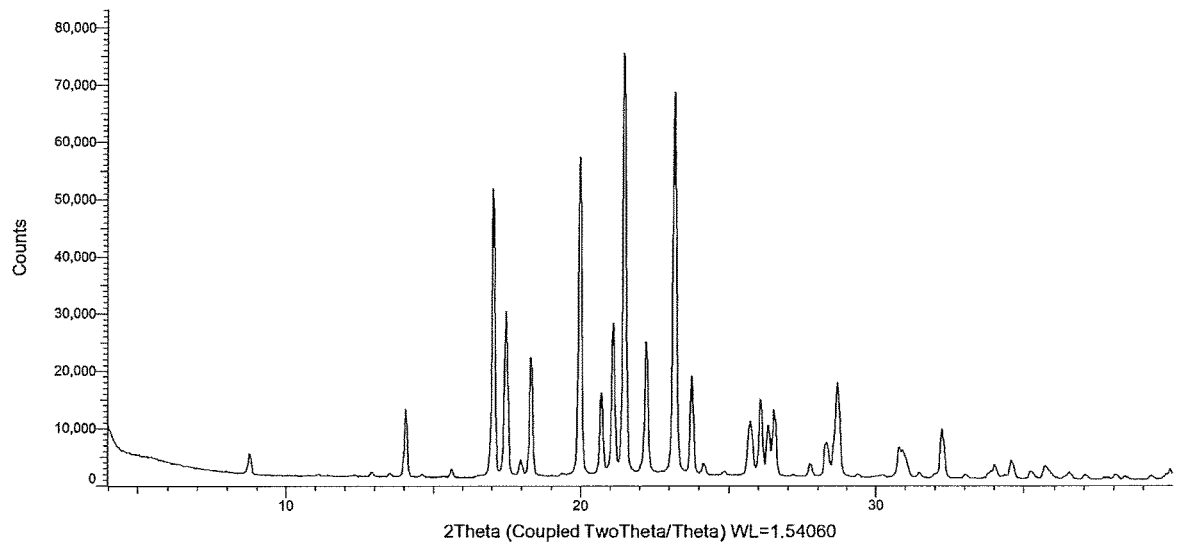
FIG. 8 depicts an XRPD diffractogram of the Form 1 polymorph of N-ethyl-2-(5-fluoro-1H-indol-3-yl)-N-methylethan-1-amine monofumarate.

N-ethyl-2-(5-fluoro-1H-indolyl-3-yl)-N-methylethan-1-amine monofumarate Form 1 was also prepared as follows. To N-ethyl-2-(5-fluoro-1H-indol-3-yl)-N-methylethan-1-amine free base dissolved in 3 volumes of ethanol solvent at about 50° C., was added 1.1 mole equivalents of fumaric acid in 0.3 volume of ethanol. After stirring for about 20 mins, the mixture was cooled to about 25° C. N-ethyl-2-(5-fluoro-1H-indol-3-yl)-N-methylethan-1-amine mono-fumarate Form 1 crystal seeds (obtained from past preparations such as the reactive crystallization screening experiments described above) are introduced and the mixture was stirred at about 25° C. About 8 volumes of isopropyl alcohol was added dropwise before the solution was further cooled to 0±5° C. and aged for about 8 hours. The crystals obtained by filtration are washed with isopropyl alcohol, and the wet cake was dried in an oven at about 45° C. This material was analyzed by XRPD and the result of which is depicted in FIG. 8. The values of the peaks and relative intensity are provided in Table 8 below.

TABLE 8

XRPD peak table of monofumarate Form 1

| Angle (° 2θ) | d-spacing (Å) | Relative intensity |
|---|---|---|
| 8.74 | 10.11 | 3 |
| 12.91 | 6.85 | 1 |
| 13.50 | 6.55 | 1 |
| 14.06 | 6.30 | 12 |
| 14.61 | 6.06 | 1 |
| 15.63 | 5.66 | 1 |
| 17.03 | 5.20 | 68 |
| 17.46 | 5.08 | 36 |
| 17.97 | 4.93 | 3 |
| 18.30 | 4.84 | 27 |
| 19.97 | 4.44 | 76 |
| 20.69 | 4.29 | 18 |
| 21.09 | 4.21 | 33 |
| 21.47 | 4.14 | 100 |
| 22.22 | 4.00 | 30 |
| 23.18 | 3.83 | 89 |
| 23.75 | 3.74 | 22 |
| 24.16 | 3.68 | 2 |
| 24.87 | 3.58 | 1 |
| 25.73 | 3.46 | 12 |
| 26.07 | 3.42 | 18 |
| 26.33 | 3.38 | 12 |
| 26.53 | 3.36 | 15 |
| 27.73 | 3.21 | 3 |
| 28.30 | 3.15 | 8 |
| 28.67 | 3.11 | 22 |
| 29.37 | 3.04 | 1 |
| 30.79 | 2.90 | 7 |
| 30.90 | 2.89 | 6 |
| 31.47 | 2.84 | 1 |
| 32.22 | 2.78 | 10 |
| 33.01 | 2.71 | 1 |
| 34.01 | 2.63 | 3 |
| 34.57 | 2.59 | 4 |
| 35.22 | 2.55 | 2 |
| 35.69 | 2.51 | 3 |
| 36.51 | 2.46 | 1 |
| 37.03 | 2.43 | 1 |
| 38.06 | 2.36 | 1 |
| 39.29 | 2.29 | 1 |

Note.
Cut-off for relative intensity was 1.

As shown, the N-ethyl-2-(5-fluoro-1H-indol-3-yl)-N-methylethan-1-amine mono-fumarate Form 1 is characterized by an X-ray powder diffraction pattern measured using Cu K-alpha radiation comprising peaks at 19.97±0.50, 21.47±0.50, and 23.18±0.50° 2θ, with the most intense peak at 21.47±0.0° 2θ. In another embodiment, the N-ethyl-2-(5-fluoro-1H-indol-3-yl)-N-methylethan-1-amine mono-fumarate Form 1 is characterized by an X-ray powder diffraction pattern measured using Cu K-alpha radiation comprising peaks at 17.03±0.50, 17.46±0.50, 19.97±0.50, 21.47±0.50, and 23.18±0.50 degrees 2θ. In a further embodiment, the N-ethyl-2-(5-fluoro-1H-indol-3-yl)-N-methylethan-1-amine mono-fumarate Form 1 is characterized by an X-ray powder diffraction pattern measured using Cu K-alpha radiation comprising peaks at 17.03±0.50, 17.46±0.50, 18.30±0.50, 19.97±0.50, 21.09±0.50, 21.47±0.50, 22.22±0.50, 23.18±0.50, 23.75±0.50, and 28.67±0.50 degrees 2θ. In a still further embodiment, the N-ethyl-2-(5-fluoro-1H-indol-3-yl)-N-methylethan-1-amine mono-fumarate Form 1 is characterized by an X-ray powder diffraction pattern measured using Cu K-alpha radiation comprising peaks at 8.74±0.50, 12.91±0.50, 13.50±0.50, 14.06±0.50, 14.61±0.50, 15.63±0.50, 17.03±0.50, 17.46±0.50, 17.97±0.50, 18.30±0.50, 19.97±0.50, 20.69±0.50, 21.09±0.50, 21.47±0.50, 22.22±0.50, 23.18±0.50, 23.75±0.50, 24.16±0.50, 24.87±0.50, 25.73±0.50, 26.07±0.50, 26.33±0.50, 26.53±0.50, 27.73±0.50, 28.30±0.50, 28.67±0.50, 29.37±0.50, 30.79±0.50, 30.90±0.50, 31.47±0.50, 32.22±0.50, 33.01±0.50, 34.01±0.50, 34.57±0.50, 35.22±0.50, 35.69±0.50, 36.51±0.50, 37.03±0.50, 38.06±0.50, and 39.29±0.50 degrees 2θ.

Figure 9:
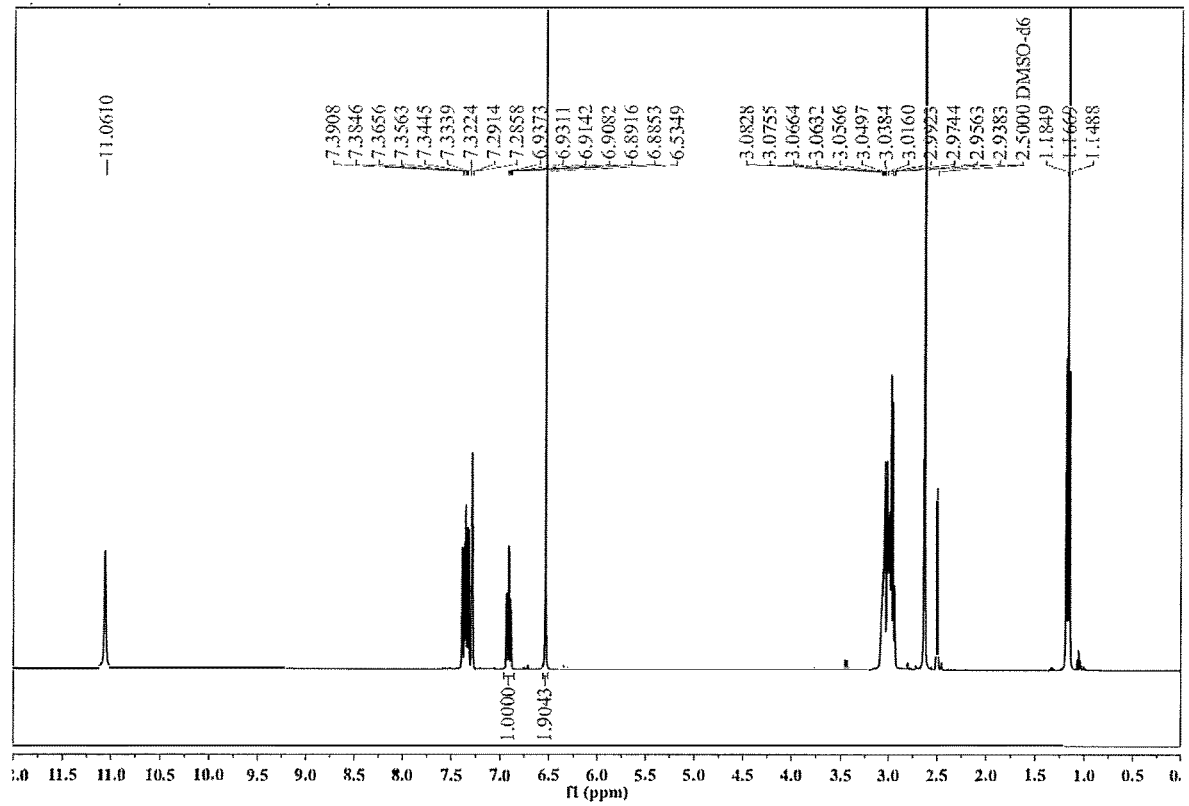
FIG. 9 depicts an $^1$H NMR spectrum (300 MHz, DMSO-$d_6$) of N-ethyl-2-(5-fluoro-1H-indol-3-yl)-N-methylethan-1-amine monofumarate Form 1.

The NMR of monofumarate Form 1 is depicted In FIG. 9.

Figure 10:
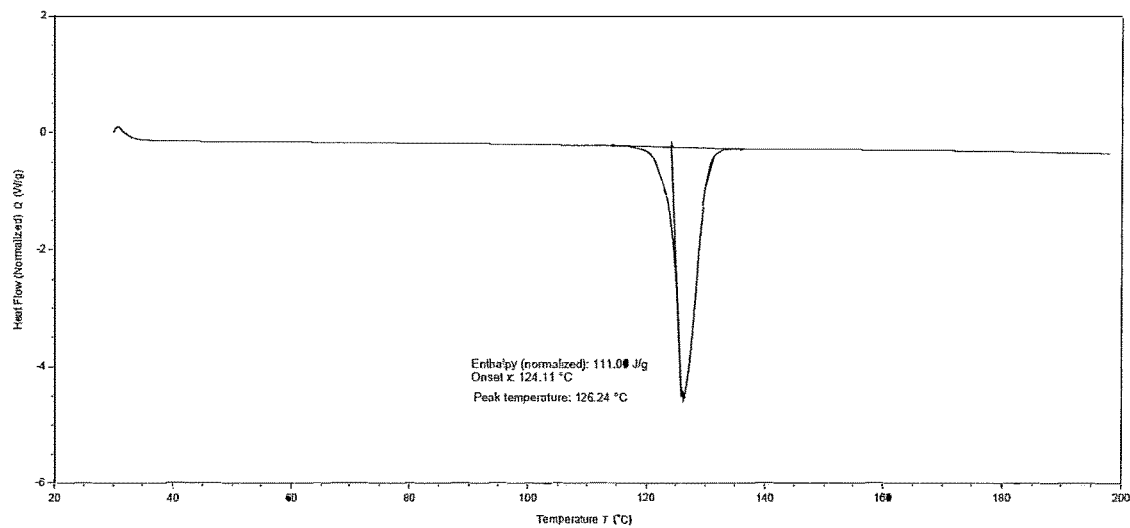
FIG. 10 depicts a DSC thermogram of the Form 1 polymorph of N-ethyl-2-(5-fluoro-1H-indol-3-yl)-N-methylethan-1-amine mono-fumarate.

The DSC thermogram of this product was recorded according to the parameters hereinabove. The resulting DSC thermogram is depicted in FIG. 10. It shows a sharp peak temperature at about 126° C.

C. N-ethyl-2-(5-fluoro-1H-indol-3-yl)-N-methylethan-1-amine Monofumarate Form 2

N-ethyl-2-(5-fluoro-1H-indol-3-yl)-N-methylethan-1-amine monofumarate Form 2 was prepared as follows. N-ethyl-2-(5-fluoro-1H-indol-3-yl)-N-methylethan-1-amine free base and 1.1 equivalent of fumaric acid were mixed in 10 volumes of isopropyl alcohol and heated to 45° C. with stirring. After 2 hours, the temperature was reduced to room temperature, and the contents were stirred overnight. A white slurry resulted and the solids were collected by filtration. A sample of the resulting crystalline N-ethyl-2-(5-fluoro-1H-indol-3-yl)-N-methylethan-1-amine monofumarate Form 2 was analyzed by XRPD, with the result depicted in FIG. 11. The values of the peaks and relative intensity are provided in Table 9 below.

TABLE 9

XRPD peak table of monofumarate Form 2

| Angle (° 2θ) | d-spacing (Å) | Relative intensity |
|---|---|---|
| 7.09 | 12.46 | 35 |
| 10.59 | 8.34 | 4 |
| 11.05 | 8.00 | 20 |
| 11.24 | 7.87 | 37 |
| 11.80 | 7.49 | 20 |
| 12.65 | 6.99 | 4 |
| 12.91 | 6.85 | 4 |
| 13.28 | 6.66 | 8 |
| 13.60 | 6.51 | 8 |
| 14.08 | 6.29 | 2 |
| 14.75 | 6.00 | 4 |
| 15.09 | 5.86 | 4 |
| 15.37 | 5.76 | 6 |
| 16.26 | 5.45 | 3 |
| 17.43 | 5.08 | 19 |
| 17.80 | 4.98 | 6 |
| 18.05 | 4.91 | 5 |
| 18.59 | 4.77 | 4 |
| 19.99 | 4.44 | 1 |
| 21.12 | 4.20 | 100 |
| 21.90 | 4.05 | 3 |

TABLE 9-continued

XRPD peak table of monofumarate Form 2

| Angle (° 2θ) | d-spacing (Å) | Relative intensity |
|---|---|---|
| 22.46 | 3.96 | 7 |
| 23.12 | 3.84 | 72 |
| 23.73 | 3.75 | 30 |
| 24.95 | 3.57 | 15 |
| 25.12 | 3.54 | 17 |
| 26.59 | 3.35 | 5 |
| 27.03 | 3.30 | 4 |
| 27.42 | 3.25 | 3 |
| 28.25 | 3.16 | 89 |

Note.
Cut-off for relative intensity was 1.

As shown, the N-ethyl-2-(5-fluoro-1H-indol-3-yl)-N-methylethan-1-amine monofumarate Form 2 is characterized by an X-ray powder diffraction pattern measured using Cu K-alpha radiation comprising peaks at 21.12±0.50, 23.12±0.50, and 28.25±0.50° 2θ, with the most intense peak at 21.12±0.50° 2θ. In another embodiment, the N-ethyl-2-(5-fluoro-1H-indol-3-yl)-N-methylethan-1-amine monofumarate Form 2 is characterized by an X-ray powder diffraction pattern measured using Cu K-alpha radiation comprising peaks at 7.09±0.50, 11.24±0.50, 21.12±0.50, 23.12±0.50, and 28.25±0.50 degrees 2θ. In a further embodiment, the N-ethyl-2-(5-fluoro-1H-indol-3-yl)-N-methylethan-1-amine monofumarate Form 2 is characterized by an X-ray powder diffraction pattern measured using Cu K-alpha radiation comprising peaks at 7.09±0.50, 11.05±0.50, 11.24±0.50, 11.80±0.50, 17.43±0.50, 21.12±0.50, 23.12±0.50, 23.73±0.50, 25.12±0.50, and 28.25±0.50 degrees 2θ. In a still further embodiment, the N-ethyl-2-(5-fluoro-1H-indol-3-yl)-N-methylethan-1-amine monofumarate Form 2 is characterized by an X-ray powder diffraction pattern measured using Cu K-alpha radiation comprising peaks at 7.09±0.50, 10.59±0.50, 11.05±0.50, 11.24±0.50, 11.80±0.50, 12.65±0.50, 12.91±0.50, 13.28±0.50, 13.60±0.50, 14.08±0.50, 14.75±0.50, 15.09±0.50, 15.37±0.50, 16.26±0.50, 17.43±0.50, 17.80±0.50, 18.05±0.50, 18.59±0.50, 19.99±0.50, 21.12±0.50, 21.90±0.50, 22.46±0.50, 23.12±0.50, 23.73±0.50, 24.95±0.50, 25.12±0.50, 26.59±0.50, 27.03±0.50, 27.42±0.50, and 28.25±0.50 degrees 2θ.

Figure 12:
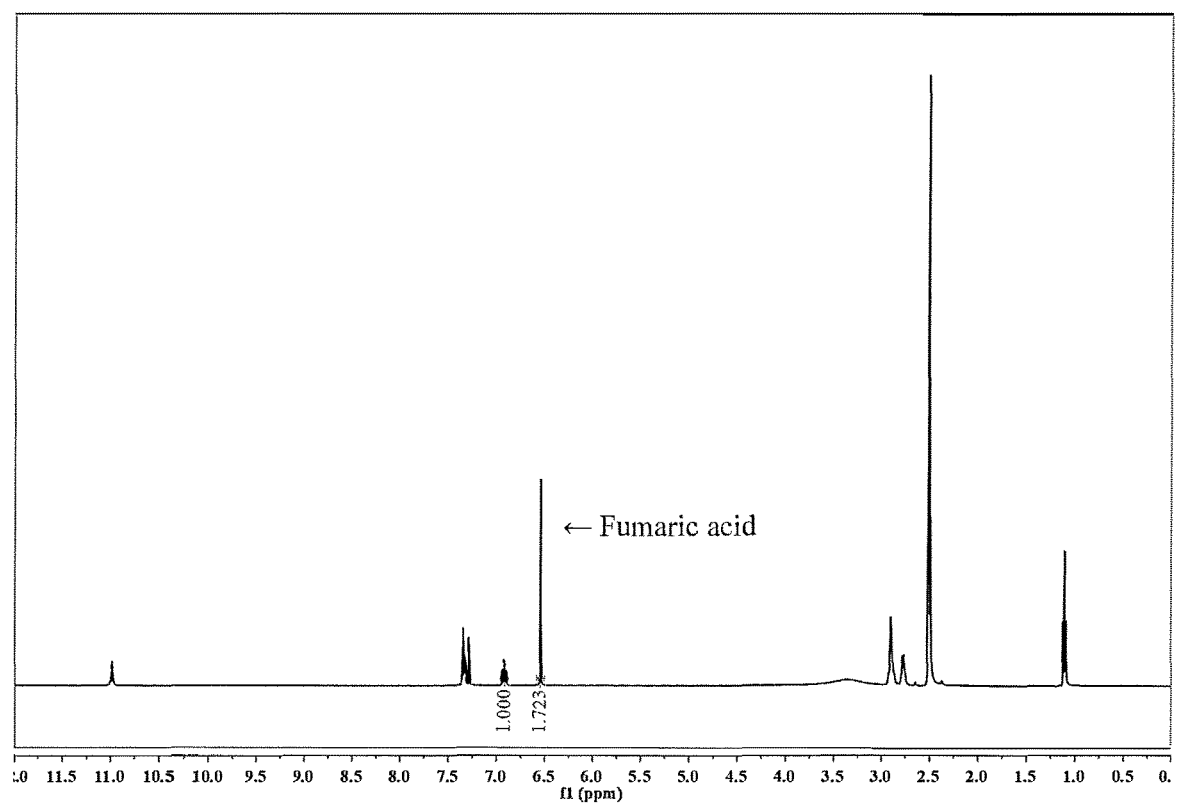
FIG. 12 depicts an $^1$H NMR spectrum (300 MHz, DMSO-$d_6$) of N-ethyl-2-(5-fluoro-1H-indol-3-yl)-N-methylethan-1-amine monofumarate Form 2.

The NMR of monofumarate Form 2 is depicted in FIG. 12.

Figure 13:
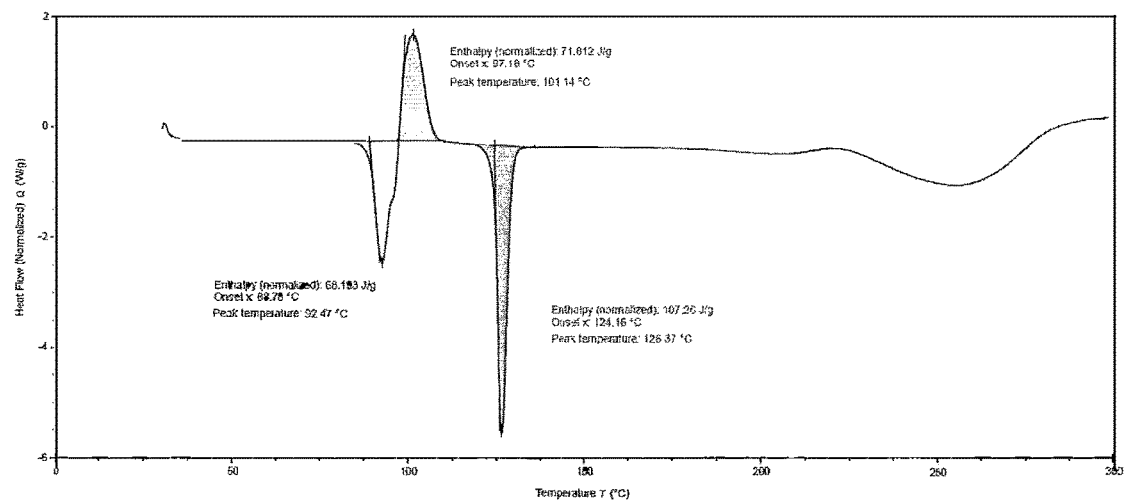
FIG. 13 depicts a DSC thermogram of the Form 2 polymorph of N-ethyl-2-(5-fluoro-1H-indol-3-yl)-N-methylethan-1-amine monofumarate.

The DSC thermogram of monofumarate Form 2 was collected according to the parameters described hereinabove, with the result depicted in FIG. 13. It depicts three peak temperatures; a peak at about 92° C., another peak at about 101° C., and final peak at about 126° C.

D. N-ethyl-2-(5-fluoro-1H-indol-3-yl)-N-methyl-ethan-1-amine Hemifumarate Form 1

The polymorphic Form 1 of N-ethyl-2-(5-fluoro-1H-indol-3-yl)-N-methylethan-1-amine hemifumarate was discovered by reactive crystallization from various solvents. These crystallization experiments were performed by subjecting the in-situ created salt, made by evaporating an ethanol solution of free base and 0.55 equivalents of fumaric acid, to vigorous agitation in 10 volumes of the selected solvent. The agitated mixtures were heated to 45-50° C. and cooled to room temperature as necessary to induce crystallization. Only one form was observed from the brief crystallization screening study, as depicted in Table 10 below.

TABLE 10

Polymorphs of N-ethyl-2-(5-fluoro-1H-indol-3-y1)-N-methylethan-1-amine hemi-fumarate obtained by reactive crystallization from different solvents

| | | XRPD pattern | | |
|---|---|---|---|---|
| Counter-ion | Solvent | Wet | Dry | Humid |
| Fumaric acid (0.55 eq.) | EtOH: MTBE (1:1 vol.) | Form 1 | Form 1 | deliquescent |
| | IPA | Form 1 | Form 1 | — |
| | Acetone | Form 1 | — | — |

Additional samples of N-ethyl-2-(5-fluoro-1H-indol-3-yl)-N-methylethan-1-amine hemifumarate Form 1 were prepared as follows. Freebase N-ethyl-2-(5-fluoro-1H-indolyl-3-yl)-N-methylethan-1-amine was combined with a solution of fumaric acid (0.56 mole eq.) in IPA (10 vol.) and the mixture was stirred at 45° C. for 17 minutes, at which point a flowable, off-white slurry was observed. The slurry was seeded with a micro-spatula tip of N-ethyl-2-(5-fluoro-1H-indol-3-yl)-N-methylethan-1-amine hemifumarate Form 1 prepared from the reactive crystallization experiments discussed above, and the mixture was stirred for another two hours at 45° C., and then cooled to room temperature and stirred overnight. The resulting crystalline solids were collected by filtration, washed with IPA, and dried. The solids were characterized by XRPD and found to be N-ethyl-2-(5-fluoro-1H-indol-3-yl)-N-methylethan-1-amine hemifumarate Form 1 with the XRPD pattern shown in FIG. 14. The values of the peaks and relative intensity are provided in Table 11 below.

TABLE 11

XRPD peak table of hemifumarate Form 1

| Angle (° 2θ) | d-spacing (Å) | Relative intensity |
|---|---|---|
| 5.79 | 15.26 | 100 |
| 10.94 | 8.08 | 23 |
| 11.55 | 7.65 | 65 |
| 12.13 | 7.29 | 9 |
| 12.60 | 7.02 | 19 |
| 15.56 | 5.69 | 9 |
| 16.28 | 5.44 | 50 |
| 17.35 | 5.11 | 33 |
| 17.96 | 4.93 | 65 |
| 18.49 | 4.80 | 57 |
| 18.86 | 4.70 | 22 |
| 19.23 | 4.61 | 39 |
| 19.53 | 4.54 | 8 |
| 20.97 | 4.23 | 30 |
| 21.32 | 4.16 | 9 |
| 21.58 | 4.11 | 37 |
| 21.95 | 4.05 | 8 |
| 22.10 | 4.02 | 9 |
| 22.48 | 3.95 | 65 |
| 23.59 | 3.77 | 38 |
| 24.17 | 3.68 | 5 |
| 24.38 | 3.65 | 7 |
| 25.10 | 3.54 | 3 |
| 25.32 | 3.52 | 3 |
| 25.78 | 3.45 | 2 |
| 26.13 | 3.41 | 7 |
| 26.60 | 3.35 | 18 |
| 27.01 | 3.30 | 9 |
| 27.46 | 3.25 | 9 |
| 28.70 | 3.11 | 3 |
| 29.44 | 3.03 | 1 |
| 29.70 | 3.00 | 1 |
| 30.20 | 2.96 | 3 |
| 31.43 | 2.84 | 2 |

TABLE 11-continued

XRPD peak table of hemifumarate Form 1

| Angle (° 2θ) | d-spacing (Å) | Relative intensity |
|---|---|---|
| 32.29 | 2.77 | 3 |
| 33.96 | 2.64 | 2 |
| 34.18 | 2.62 | 3 |
| 35.08 | 2.56 | 2 |
| 36.93 | 2.43 | 1 |
| 37.93 | 2.37 | 2 |
| 38.97 | 2.30 | 1 |

Note.
Cut-off for relative intensity was 1.

As shown, the N-ethyl-2-(5-fluoro-1H-indol-3-yl)-N-methylethan-1-amine hemifumarate Form 1 is characterized by an X-ray powder diffraction pattern measured using Cu K-alpha radiation comprising peaks at 5.79±0.50, 11.55±0.50, 17.96±0.50, and 22.48±0.50° 2θ, with the most intense peak at 5.79±0.50° 2θ. In an embodiment, the N-ethyl-2-(5-fluoro-1H-indol-3-yl)-N-methylethan-1-amine hemifumarate Form 1 is characterized by an X-ray powder diffraction pattern measured using Cu K-alpha radiation comprising peaks at 5.79±0.50, 11.55±0.50, 17.96±0.50, 18.49±0.50, and 22.48±0.50 degrees 2θ. In a further embodiment, the N-ethyl-2-(5-fluoro-1H-indol-3-yl)-N-methylethan-1-amine hemifumarate Form 1 is further characterized by an X-ray powder diffraction pattern measured using Cu K-alpha radiation comprising peaks at 5.79±0.50, 11.55±0.50, 16.28±0.50, 17.35±0.50, 17.96±0.50, 18.49±0.50, 19.23±0.50, 21.58±0.50, 22.48±0.50, and 23.59±0.50 degrees 2θ. In a still further embodiment, the N-ethyl-2-(5-fluoro-1H-indol-3-yl)-N-methylethan-1-amine hemifumarate Form 1 is further characterized by an X-ray powder diffraction pattern measured using Cu K-alpha radiation comprising peaks at 5.79±0.50, 10.94±0.50, 11.55±0.50, 12.13±0.50, 12.60±0.50, 15.56±0.50, 16.28±0.50, 17.35±0.50, 17.96±0.50, 18.49±0.50, 18.86±0.50, 19.23±0.50, 19.53±0.50, 20.97±0.50, 21.32±0.50, 21.58±0.50, 21.95±0.50, 22.10±0.50, 22.48±0.50, 23.59±0.50, 24.17±0.50, 24.38±0.50, 25.10±0.50, 25.32±0.50, 25.78±0.50, 26.13±0.50, 26.60±0.50, 27.01±0.50, 27.46±0.50, 28.70±0.50, 29.44±0.50, 29.70±0.50, 30.20±0.50, 31.43±0.50, 32.29±0.50, 33.96±0.50, 34.18±0.50, 35.08±0.50, 36.93±0.50, 37.93±0.50, and 38.97±0.50 degrees 2θ.

Figure 15:
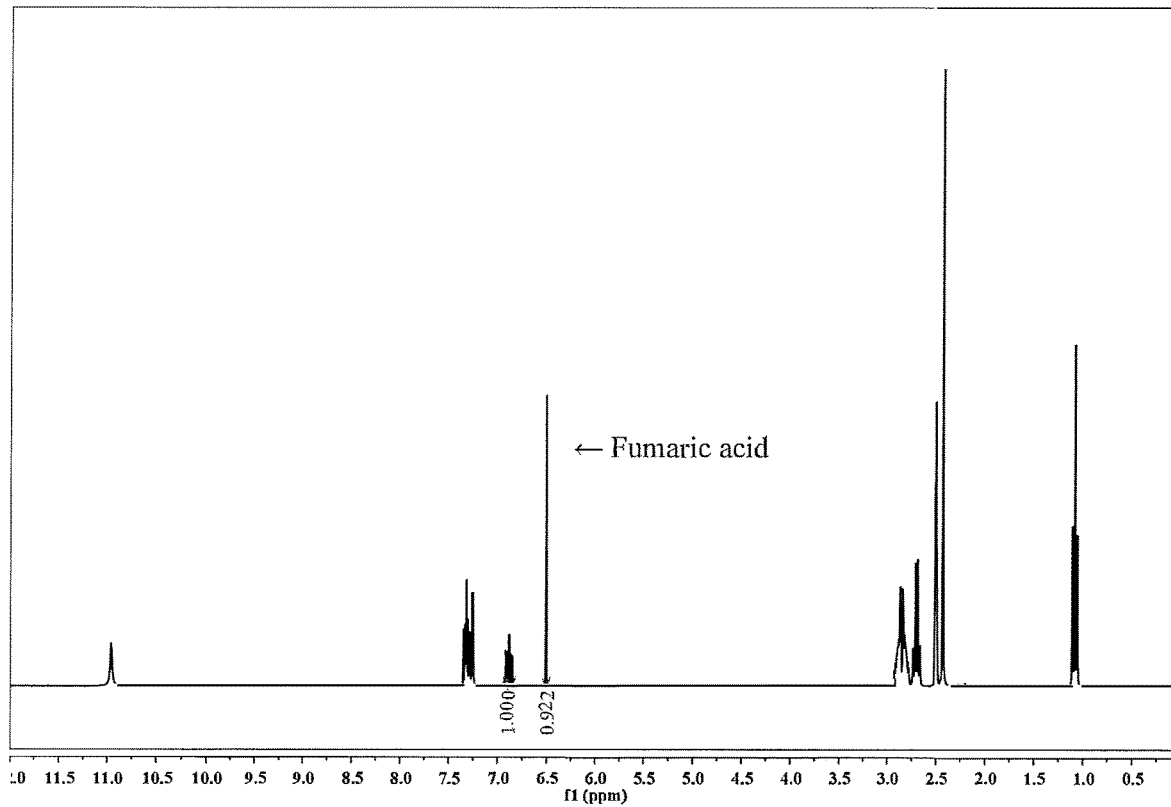
FIG. 15 depicts an $^1$H NMR spectrum (300 MHz, DMSO-$d_6$) of N-ethyl-2-(5-fluoro-1H-indol-3-yl)-N-methylethan-1-amine hemifumarate Form 1.

The NMR of hemifumarate Form 1 is depicted in FIG. 15.

Figure 16:
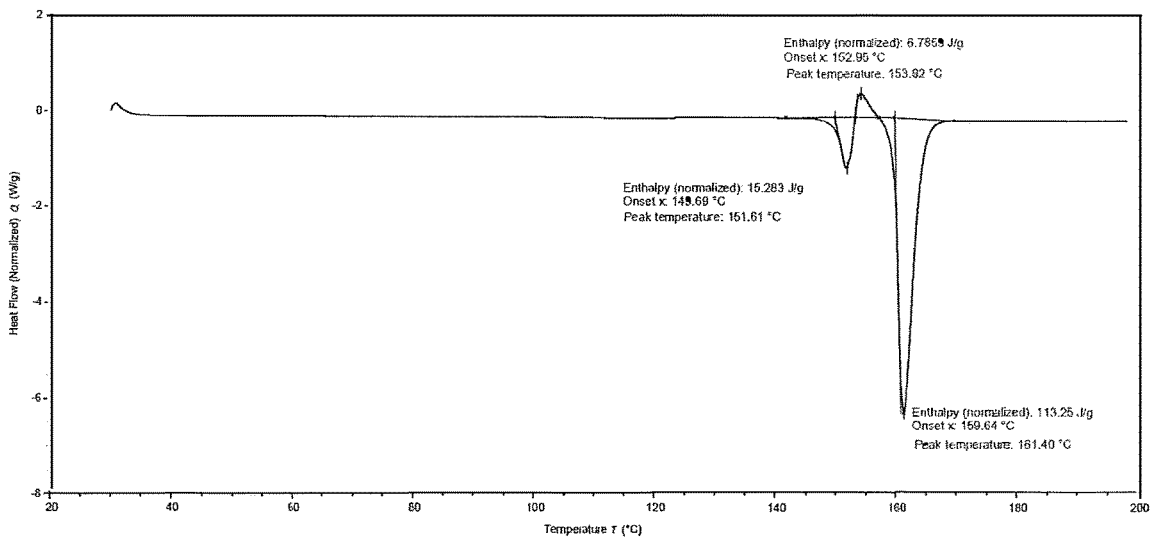
FIG. 16 depicts a DSC thermogram of the Form 1 polymorph of N-ethyl-2-(5-fluoro-1H-indol-3-yl)-N-methylethan-1-amine hemifumarate.

The DSC thermogram of hemifumarate Form 1 was collected according to the parameters described hereinabove, with the result depicted in FIG. 16. The DSC thermogram exhibits three temperature peaks, a small one at about 15 2° C., a smaller one at about 154° C., and a significantly larger one at about 161° C.

E. N-ethyl-2-(5-fluoro-1H-indol-3-yl)-N-methylethan-1-amine Hemifumarate Form 2

Figure 17:
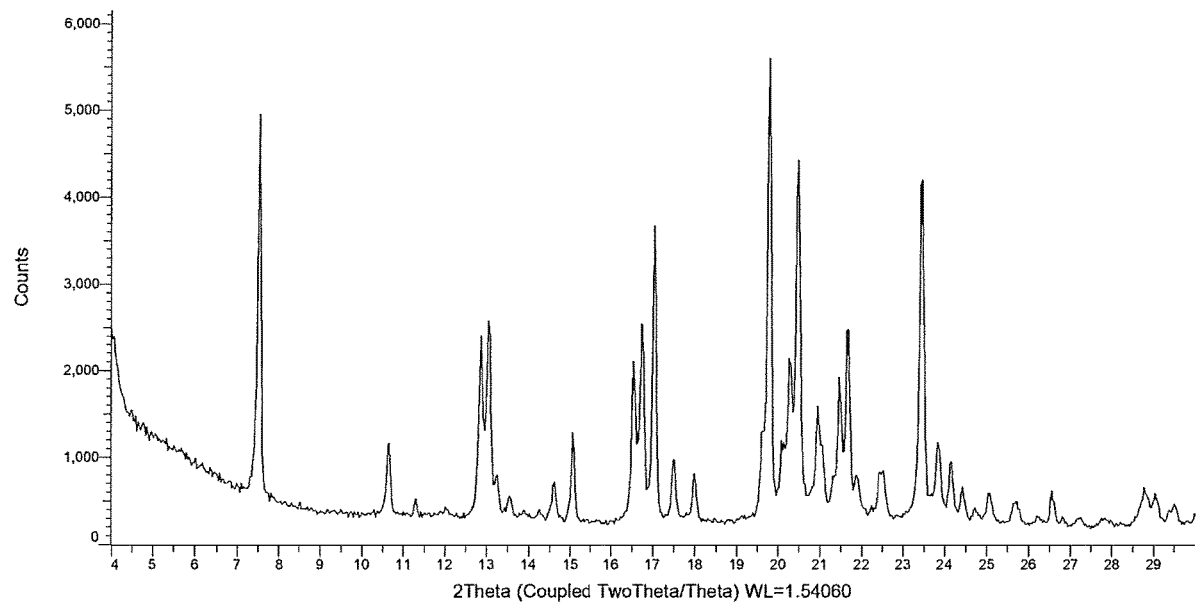
FIG. 17 depicts an XRPD diffractogram of the Form 2 polymorph of N-ethyl-2-(5-fluoro-1H-indol-3-yl)-N-methylethan-1-amine hemifumarate.

Hemifumarate Form 2 is prepared by melting solid N-ethyl-2-(5-fluoro-1H-indol-3-yl)-N-methylethan-1-amine hemifumarate Form 1. The spontaneous crystallization of the melted liquid under DSC testing conditions formed a different polymorph, N-ethyl-2-(5-fluoro-1H-indol-3-yl)-N-methylethan-1-amine hemifumarate Form 2. A sample of N-ethyl-2-(5-fluoro-1H-indol-3-yl)-N-methylethan-1-amine hemifumarate Form 2 was analyzed by XRPD, the result of which is depicted in FIG. 17. The values of the peaks and relative intensity are provided in Table 12 below:

TABLE 12

Peak table of hemifumarate Form 2

| Angle (° 2θ) | d-spacing (Å) | Relative intensity |
|---|---|---|
| 7.54 | 11.72 | 68 |
| 10.64 | 8.31 | 14 |
| 11.29 | 7.83 | 3 |
| 12.01 | 7.36 | 2 |
| 12.86 | 6.88 | 36 |
| 13.05 | 6.78 | 38 |
| 13.24 | 6.68 | 8 |
| 13.55 | 6.53 | 4 |
| 13.89 | 6.37 | 1 |
| 14.25 | 6.21 | 2 |
| 14.60 | 6.06 | 7 |
| 15.06 | 5.88 | 19 |
| 16.54 | 5.36 | 33 |
| 16.74 | 5.29 | 41 |
| 17.04 | 5.20 | 64 |
| 17.49 | 5.07 | 13 |
| 17.98 | 4.93 | 10 |
| 19.12 | 4.64 | 1 |
| 19.60 | 4.53 | 24 |
| 19.78 | 4.49 | 100 |
| 20.08 | 4.42 | 17 |
| 20.27 | 4.38 | 34 |
| 20.46 | 4.34 | 77 |
| 20.94 | 4.24 | 24 |
| 21.04 | 4.22 | 14 |
| 21.33 | 4.16 | 8 |
| 21.47 | 4.14 | 31 |
| 21.66 | 4.10 | 43 |
| 21.87 | 4.06 | 9 |
| 22.23 | 4.00 | 2 |
| 22.44 | 3.96 | 9 |
| 23.43 | 3.79 | 78 |
| 23.84 | 3.73 | 17 |
| 24.14 | 3.68 | 12 |
| 24.42 | 3.64 | 7 |
| 24.71 | 3.60 | 3 |
| 25.06 | 3.55 | 6 |
| 25.71 | 3.46 | 4 |
| 26.20 | 3.40 | 2 |
| 26.55 | 3.35 | 9 |
| 26.82 | 3.32 | 2 |
| 27.25 | 3.27 | 1 |
| 27.83 | 3.20 | 1 |
| 28.77 | 3.10 | 8 |
| 29.03 | 3.07 | 7 |
| 29.38 | 3.04 | 3 |
| 29.50 | 3.03 | 4 |

Note.
Cut-off for relative intensity was 1.

As shown, in an embodiment, the N-ethyl-2-(5-fluoro-1H-indol-3-yl)-N-methylethan-1-amine hemifumarate Form 2 is characterized by an X-ray powder diffraction pattern measured using Cu K-alpha radiation comprising peaks at 19.78±0.50, 20.46±0.50, and 23.43±0.50° 2θ, with the most intense peak at 19.78±0.50° 2θ. In another embodiment, the N-ethyl-2-(5-fluoro-1H-indol-3-yl)-N-methylethan-1-amine hemifumarate Form 2 is characterized by an X-ray powder diffraction pattern measured using Cu K-alpha radiation comprising peaks at 7.54±0.50, 17.04±0.50, 19.78±0.50, 20.46±0.50, and 23.43±0.50 degrees 2θ. In a further embodiment, the N-ethyl-2-(5-fluoro-1H-indol-3-yl)-N-methylethan-1-amine hemifumarate Form 2 is characterized by an X-ray powder diffraction pattern measured using Cu K-alpha radiation comprising peaks at 7.54±0.50, 12.86±0.50, 13.05±0.50, 16.74±0.50, 17.04±0.50, 19.78±0.50, 20.27±0.50, 20.46±0.50, 21.66±0.50, and 23.43±0.50 degrees 2θ. In a still further embodiment, the N-ethyl-2-(5-fluoro-1H-indol-3-yl)-N-methylethan-1-amine hemifumarate Form 2 is characterized by an X-ray powder diffraction pattern measured using Cu K-alpha radiation comprising peaks at 7.54±0.50, 10.64±0.50, 11.29±0.50, 12.01±0.50, 12.86±0.50, 13.05±0.50, 13.24±0.50, 13.55±0.50, 13.89±0.50, 14.25±0.50, 14.60±0.50, 15.06±0.50, 16.54±0.50, 16.74±0.50, 17.04±0.50, 17.49±0.50, 17.98±0.50, 19.12±0.50, 19.60±0.50, 19.78±0.50, 20.08±0.50, 20.27±0.50, 20.46±0.50, 20.94±0.50, 21.04±0.50, 21.33±0.50, 21.47±0.50, 21.66±0.50, 21.87±0.50, 22.23±0.50, 22.44±0.50, 23.43±0.50, 23.84±0.50, 24.14±0.50, 24.42±0.50, 24.71±0.50, 25.06±0.50, 25.71±0.50, 26.20±0.50, 26.55±0.50, 26.82±0.50, 27.25±0.50, 27.83±0.50, 28.77±0.50, 29.03±0.50, 29.38±0.50, and 29.50±0.50 degrees 2θ.

Figure 18:
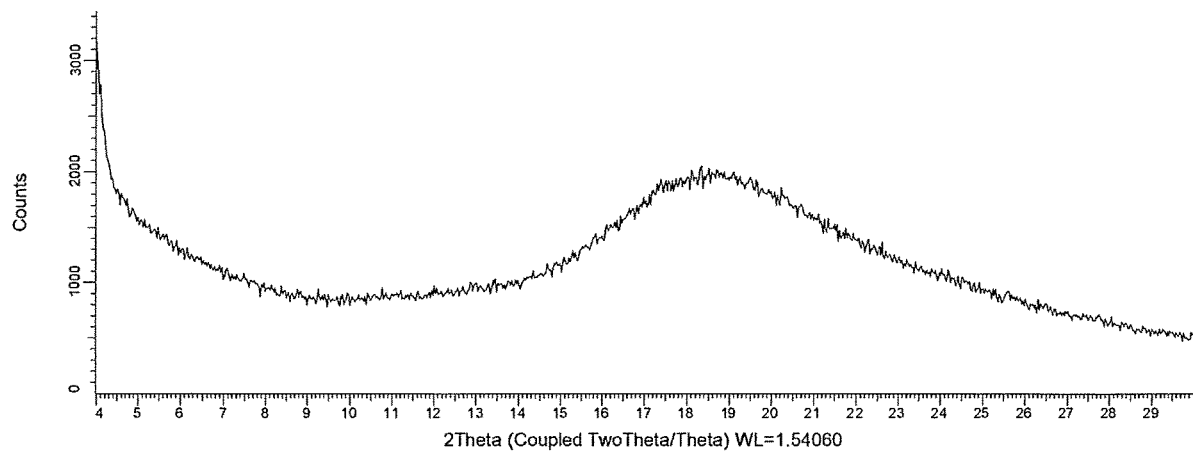
FIG. 18 depicts an XRPD diffractogram of N-ethyl-2-(5-fluoro-1H-indol-3-yl)-N-methylethan-1-amine freebase.

III. Amorphous N-ethyl-2-(5-fluoro-1H-indol-3-yl)-N-methylethan-1-amine Freebase This is prepared by basification of any of the disclosed salts of N-ethyl-2-(5-fluoro-1H-indol-3-yl)-N-methylethan-1-amine. For example, N-ethyl-2-(5-fluoro-1H-indol-3-yl)-N-methylethan-1-amine monofumarate Form 1 or Form 2 was dissolved in methyl tert-butyl ether (MTBE; 10 volumes) and neutralized with aqueous NaOH over a 2 h period until the pH was about 11. The mixture was stirred for an additional 30-45 min. Stirring was stopped, and the aqueous and organic phases were allowed to separate. The organic layer was separated and washed with saturated aqueous NaHCO$_3$ and then with distilled water. The organic phase was dried under a gentle stream of nitrogen until an amber oil was observed. The near-dry oil was further dried under vacuum overnight. A sample of this freebase was analyzed by XRPD, the result of which is depicted in FIG. 18. The lack of defined peaks indicated an amorphous material.

IV. ADDITIONAL DATA

Dynamic Vapor Sorption (DVS) was performed using a Q5000SA. The sample (5-15 mg) was loaded into a metallic quartz sample pan, suspended from a microbalance, and exposed to a humidified stream of nitrogen gas. Weight changes were relative to a matching empty reference pan opposite the sample, suspended from the microbalance. The sample was held for a minimum of 10 min at each level and only progressed to the next humidity level if there was <0.002% change in weight between measurements (interval: 5 s) or 45 min had elapsed (for 5-65% RH) or 2 h had elapsed (for 80 and 95% RH). The following programs were used:
1—Equilibration at 50% RH
2—50% to 5%. (50%, 35%, 20%, and 5%)
3—5% to 95% (5%, 20%, 35%, 50%, 65%, 80%, and 95%)
4—95% to 5% (95%, 80%, 65%, 50%, 35%, 20%, and 5%)
5—5% to 50% (5%, 20%, 35%, and 50%)
1—Equilibration at 50% RH
2—50% to 2%. (50%, 40%, 30%, 20%, 10%, and 2%)
3—2% to 75% (2%, 10%, 20%, 30%, 40%, 50%, 60%, 70% and 75%)
4—75% to 2% (75%, 70%, 60%, 50%, 40%, 30%, 20%, 10% and 2%)
5—2% to 50% (2%, 10%, 20%, 30%, 40% and 50%)
1—Equilibration at 50% RH
2—50% to 2%. (50%, 40%, 30%, 20%, 10%, and 2%)
3—2% to 65% (2%, 10%, 20%, 30%, 40%, 50%, 60% and 65%)
4—65% to 2% (65%, 60%, 50%, 40%, 30%, 20%, 10% and 2%)
5—2% to 50% (2%, 10%, 20%, 30%, 40% and 50%).

Figure 19:
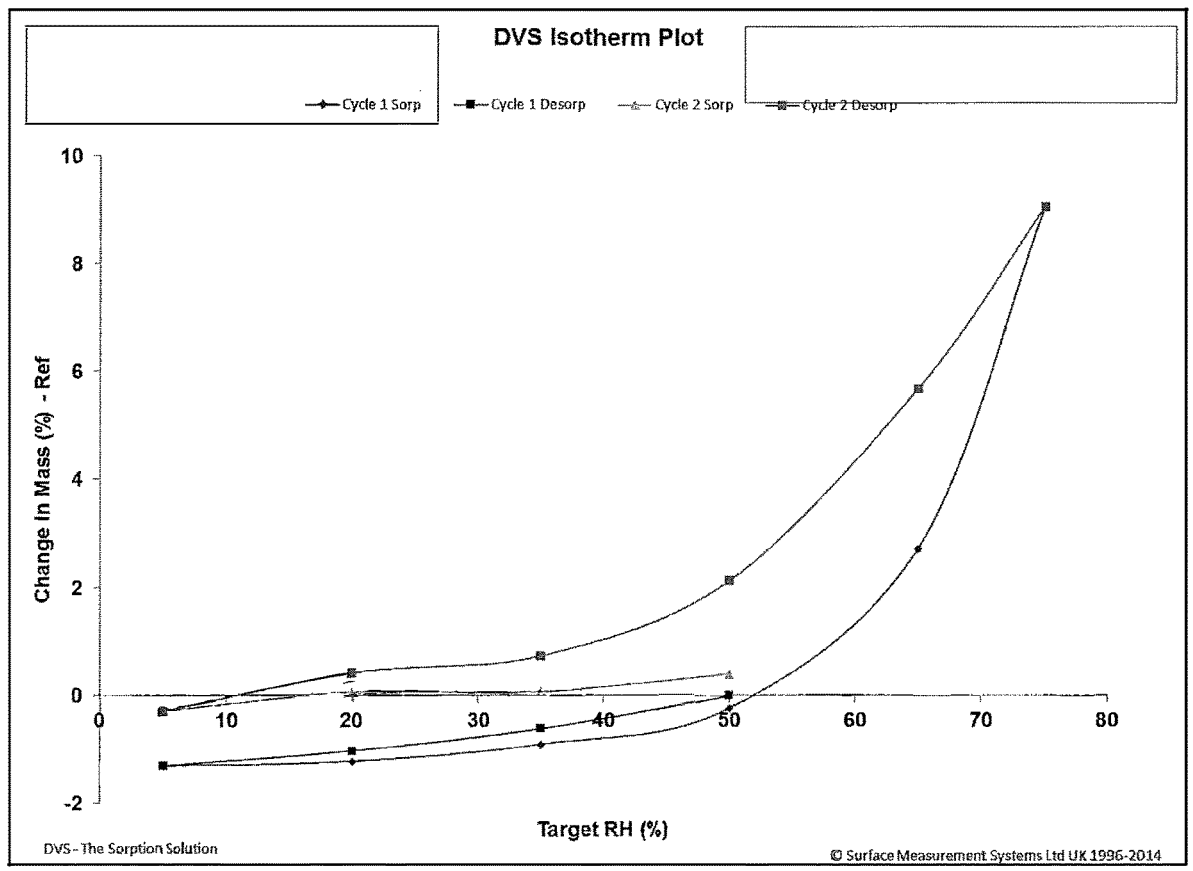
FIG. 19 is a DVS isotherm plot at 25° C. of N-ethyl-2-(5-fluoro-1H-indol-3-yl)-N-methylethan-1-amine hydrochloride Form 1.

A DVS isotherm plot at 25° C. of N-ethyl-2-(5-fluoro-1H-indol-3-yl)-N-methylethan-1-amine hydrochloride Form 1 is depicted in FIG. 19. As shown, the sample did not reach equilibrium at 75% RH.

Figure 20:
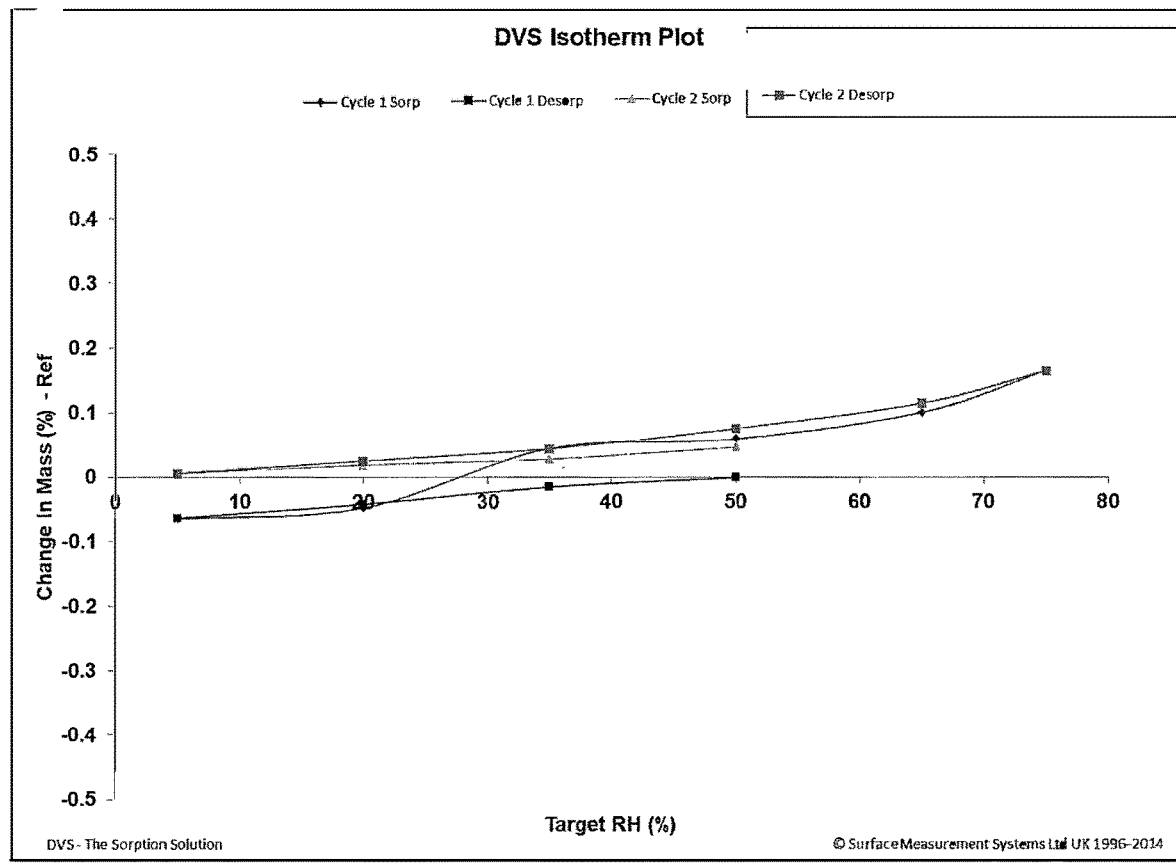
FIG. 20 is a DVS isotherm plot of N-ethyl-2-(5-fluoro-1H-indol-3-yl)-N-methylethan-1-amine hydrochloride Form 2.

A DVS isotherm plot of N-ethyl-2-(5-fluoro-1H-indol-3-yl)-N-methylethan-1-amine hydrochloride Form 2 is shown in FIG. 20.

Figure 21:
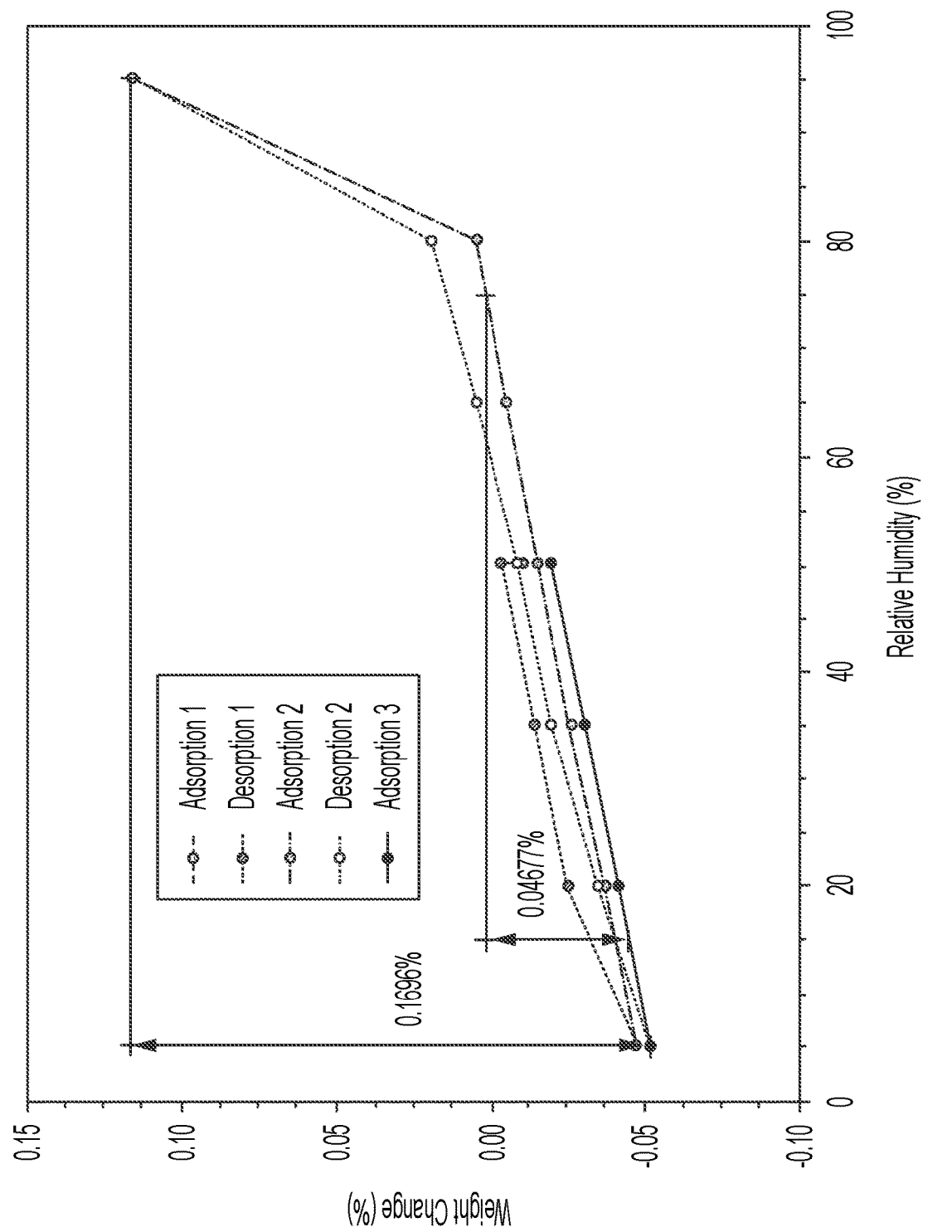
FIG. 21 is a DVS isotherm plot of N-ethyl-2-(5-fluoro-1H-indol-3-yl)-N-methylethan-1-amine fumarate Form 1.

A DVS isotherm plot of N-ethyl-2-(5-fluoro-1H-indol-3-yl)-N-methylethan-1-amine fumarate Form 1 is shown in FIG. 21.

Figure 22:
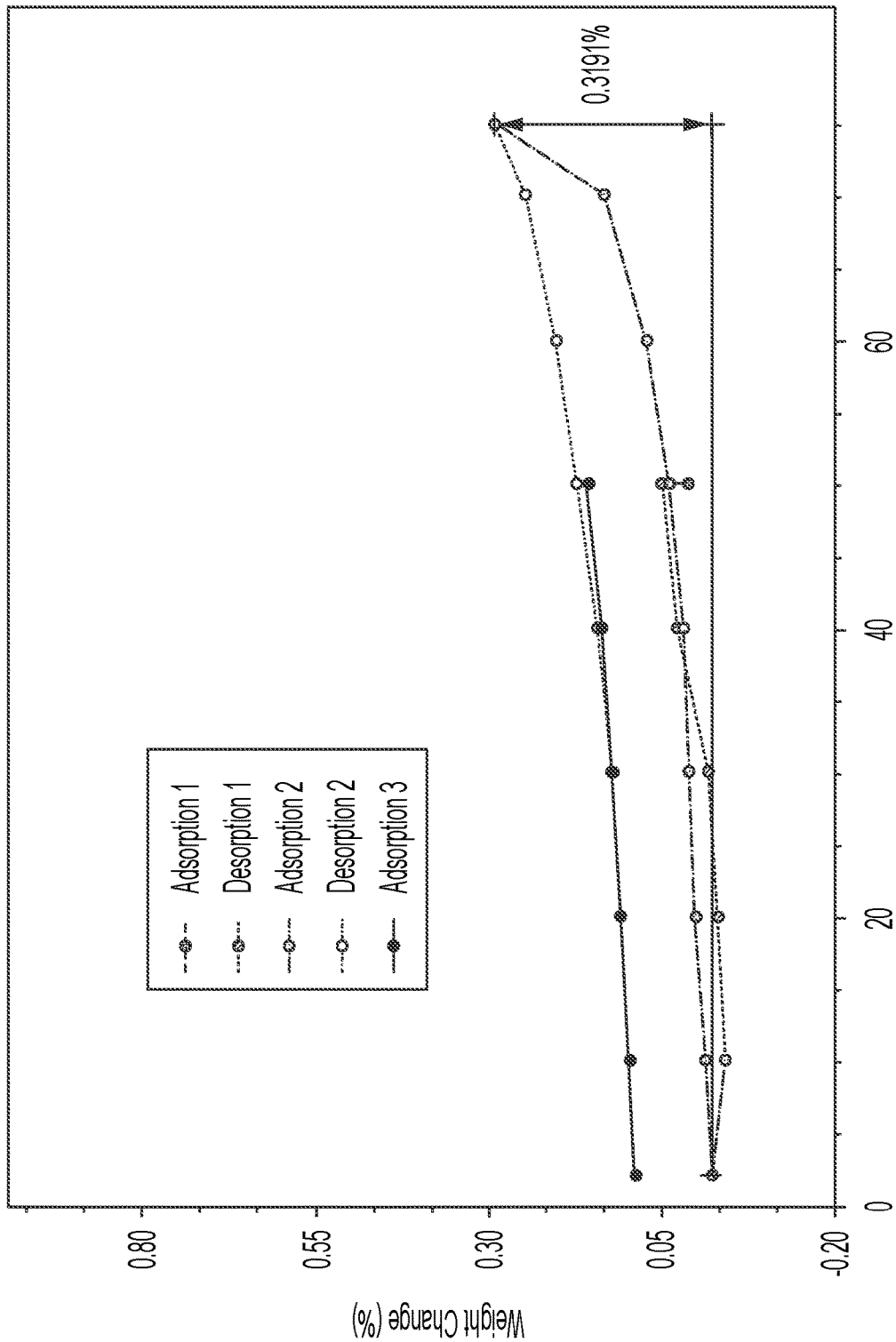
FIG. 22 is a DVS isotherm plot of N-ethyl-2-(5-fluoro-1H-indol-3-yl)-N-methylethan-1-amine hemifumarate Form 1.

A DVS isotherm plot of N-ethyl-2-(5-fluoro-1H-indol-3-yl)-N-methylethan-1-amine hemifumarate Form 1 is shown in FIG. 22.

Also described herein are methods and compositions comprised of the hydrochloride salts, fumarate salts, and freebase for treating a mood disorder by administering to a patient in need thereof a hydrochloride salt or fumarate salt or freebase disclosed herein. Also provided are pharmaceutical compositions that include a hydrochloride salt or fumarate salt or freebase disclosed herein. As used herein, the compositions made reference to include a hydrochloride salt or fumarate salt or freebase.

In embodiments, the methods and these compositions may be used to treat a mood disorder including depressive disorders, e.g., major depressive disorder, persistent depressive disorder, postpartum depression, premenstrual dysphoric disorder, seasonal affective disorder, psychotic depression, disruptive mood dysregulation disorder, substance/medication-induced depressive disorder, and depressive disorder due to another medical condition.

In some embodiments, depression conditions include major depressive disorder and dysthymic disorder. In some embodiments, depression conditions develop under unique circumstances, including, but are not limited to, psychotic depression, postpartum depression, seasonal affective disorder (SAD), mood disorder, depressions caused by chronic medical conditions such as cancer or chronic pain, chemotherapy, chronic stress, post-traumatic stress disorders, and bipolar disorder (or manic depressive disorder). In some embodiments, depression conditions that are expected to be treated according to this aspect of the present disclosure include, but are not limited to, major depressive disorder, dysthymic disorder, psychotic depression, postpartum depression, premenstrual syndrome, premenstrual dysphoric disorder, seasonal affective disorder (SAD), anxiety, mood disorder, depressions caused by chronic medical conditions such as cancer or chronic pain, chemotherapy, chronic stress, post-traumatic stress disorders, and bipolar disorder (or manic depressive disorder).

Also provided herein are methods of treating refractory depression, e.g., patients suffering from a depressive disorder that does not, and/or has not, responded to adequate courses of at least one, or at least two, other antidepressant compounds or therapeutics. For example, provided herein is a method of treating depression in a treatment resistant patient, comprising a) optionally identifying the patient as treatment resistant and b) administering an effective dose of a disclosed hydrochloride salt or fumarate salt. As used herein "depressive disorder" encompasses refractory depression. In some embodiments, refractory depression occurs in patients suffering from depression who are resistant to standard pharmacological treatments, including tricyclic antidepressants, MAOIs, SSRIs, and double and triple uptake inhibitors and/or anxiolytic drugs, as well non-pharmacological treatments such as psychotherapy, electroconvulsive therapy, vagus nerve stimulation and/or transcranial magnetic stimulation. In some embodiments, a treatment resistant-patient may be identified as one who fails to experience alleviation of one or more symptoms of depression (e.g., persistent anxious or sad feelings, feelings of helplessness, hopelessness, pessimism) despite undergoing one or more standard pharmacological or non-pharmacological treatment. In certain embodiments, a treatment-resistant patient is one who fails to experience alleviation of one or more symptoms of depression despite undergoing treatment with two different antidepressant drugs. In other embodiments, a treatment-resistant patient is one who fails to experience alleviation of one or more symptoms of depression despite undergoing treatment with four different antidepressant drugs, other than the hydrochloride salt or fumarate salt disclosed herein. In some embodiments, a treatment-resistant patient may also be identified as one who is unwilling or unable to tolerate the side effects of one or more standard pharmacological or non-pharmacological treatment.

In some embodiments, symptoms associated with depression include, but are not limited to, persistent anxious or sad feelings, feelings of helplessness, hopelessness, pessimism, and/or worthlessness, low energy, restlessness, irritability, fatigue, loss of interest in pleasurable activities or hobbies, excessive sleeping, overeating, appetite loss, insomnia, thoughts of suicide, or suicide attempts. In some embodiments, various symptoms associated with anxiety include fear, panic, heart palpitations, shortness of breath, fatigue, nausea, and headaches among others. In addition, patients suffering from any form of depression often experience anxiety. It is expected that the methods of the present condition can be used to treat anxiety or any of the symptoms thereof. In some embodiments, presence, severity, frequency, and duration of symptoms of depression vary on a case-to-case basis.

In embodiments, the methods and these compositions may be used to treat a mood disorder including bipolar and related disorders, e.g., bipolar I disorder, bipolar II disorder, cyclothymic disorder, substance/medication-induced bipolar and related disorder, and bipolar and related disorder due to another medical condition.

In embodiments, the methods and these compositions may be used to treat a mood disorder including substance-related disorders, e.g., preventing a substance use craving, diminishing a substance use craving, and/or facilitating substance use cessation or withdrawal. Substance use disorders involve abuse of psychoactive compounds such as alcohol, caffeine, *cannabis*, inhalants, opioids, sedatives, hypnotics, anxiolytics, stimulants, nicotine and tobacco. As used herein "substance" or "substances" are psychoactive compounds which can be addictive such as alcohol, caffeine, *cannabis*, hallucinogens, inhalants, opioids, sedatives, hypnotics, anxiolytics, stimulants, nicotine and tobacco. For example, the methods and compositions may be used to facilitate smoking cessation or cessation of opioid use.

In embodiments, the methods and compositions may be used to treat a mood disorder including anxiety disorders, e.g., separation anxiety disorder, selective mutism, specific phobia, social anxiety disorder (social phobia), panic disorder, panic attack, agoraphobia, generalized anxiety disorder, substance/medication-induced anxiety disorder, and anxiety disorder due to another medical condition.

In embodiments, the methods and compositions may be used to treat a mood disorder including obsessive-compulsive and related disorders, e.g., obsessive-compulsive disorder, body dysmorphic disorder, hoarding disorder, trichotillomania (hair-pulling disorder), excoriation (skin-picking) disorder, substance/medication-induced obsessive-compulsive and related disorder, and obsessive-compulsive and related disorder due to another medical condition.

In embodiments, the methods and compositions may be used to treat a mood disorder including trauma- and stressor-related disorders, e.g., reactive attachment disorder, disinhibited social engagement disorder, posttraumatic stress disorder, acute stress disorder, and adjustment disorders.

In embodiments, the methods and compositions may be used to treat a mood disorder including feeding and eating disorders, e.g., anorexia nervosa, bulimia nervosa, binge-eating disorder, pica, rumination disorder, and avoidant/restrictive food intake disorder.

In embodiments, the methods and compositions may be used to treat a mood disorder including neurocognitive disorders, e.g., delirium, major neurocognitive disorder, mild neurocognitive disorder, major or mild neurocognitive disorder due to Alzheimer's disease, major or mild frontotemporal neurocognitive disorder, major or mild neurocognitive disorder with Lewy bodies, major or mild vascular neurocognitive disorder, major or mild neurocognitive disorder due to traumatic brain injury, substance/medication-induced major or mild neurocognitive disorder, major or mild neurocognitive disorder due to HIV infection, major or mild neurocognitive disorder due to prion disease, major or mild neurocognitive disorder due to Parkinson's disease, major or mild neurocognitive disorder due to Huntington's disease, major or mild neurocognitive disorder due to another medical condition, and major or mild neurocognitive disorder due to multiple etiologies.

In embodiments, the methods and compositions may be used to treat a mood disorder including neurodevelopmental disorders, e.g., autism spectrum disorder, attention-deficit/hyperactivity disorder, stereotypic movement disorder, tic disorders, Tourette's disorder, persistent (chronic) motor or vocal tic disorder, and provisional tic disorder. In some embodiments, a variety of other neurological conditions may be treated according to the methods of the present disclosure. In some embodiments, neurological conditions include, but are not limited to, a learning disorder, autistic disorder, attention-deficit hyperactivity disorder, Tourette's syndrome, phobia, post-traumatic stress disorder, dementia, AIDS dementia, Alzheimer's disease, Parkinson's disease, spasticity, myoclonus, muscle spasm, bipolar disorder, a substance abuse disorder, urinary incontinence, and schizophrenia.

In embodiments, the methods and compositions may be used to treat a mood disorder including personality disorders, e.g., borderline personality disorder.

In embodiments, the methods and compositions may be used to treat a mood disorder including sexual dysfunctions, e.g., delayed ejaculation, erectile disorder, female orgasmic disorder, female sexual interest/arousal disorder, genito-pelvic pain/penetration disorder, male hypoactive sexual desire disorder, premature (early) ejaculation, and substance/medication-induced sexual dysfunction.

In embodiments, the methods and compositions may be used to treat a mood disorder including gender dysphoria.

In embodiments provided are methods and compositions for treating a mood disorder by administering to a subject in need thereof an effective amount of hydrochloride salt or fumarate salt or freebase described herein.

In other embodiments, provided herein are methods and compositions for treating migraine, cluster headache, or other headache disorders by administering to a patient in need thereof a hydrochloride salt or a fumarate salt or freebase of the present disclosure.

In other embodiments, provided herein are methods and compositions for treating inflammation by administering to a patient in need thereof a hydrochloride salt or fumarate salt or freebase of the present disclosure.

In embodiments, methods include treating a mood disorder, e.g., a depressive disorder, by administering to a patient in need thereof a pharmaceutical composition including about 0.01 mg to about 400 mg of a hydrochloride salt or fumarate salt or freebase disclosed herein. In embodiments, doses may be, e.g., in the range of about 0.01 to 400 mg, 0.01 to 300 mg, 0.01 to 250 mg, 0.01 to 200 mg, 0.01 to 150 mg, 0.01 to 100 mg, 0.01 to 75 mg, 0.01 to 50 mg, 0.01 to 25 mg, 0.01 to 20 mg, 0.01 to 15 mg, 0.01 to 10 mg, 0.01 to 5 mg, 0.01 to 1 mg, 0.01 to 0.5 mg, 0.01 to 0.1 mg, 0.1 to 300 mg, 0.1 to 250 mg, 0.1 to 200 mg, 0.1 to 150 mg, 0.1 to 100 mg, 0.1 to 75 mg, 0.1 to 50 mg, 0.1 to 25 mg, 0.1 to 20 mg, 0.1 to 15 mg, 0.1 to 10 mg, 0.1 to 5 mg, 0.1 to 1 mg, 10 to 300 mg, 10 to 250 mg, 10 to 200 mg, 10 to 150 mg, 10 to 100 mg, 10 to 50 mg, 10 to 25 mg, 10 to 15 mg, 20 to 300 mg, 20 to 250 mg, 20 to 200 mg, 20 to 150 mg, 20 to 100 mg, 20 to 50 mg, 50 to 300 mg, 50 to 250 mg, 50 to 200 mg, 50 to 150 mg, 50 to 100 mg, 100 to 300 mg, 100 to 250 mg, 100 to 200 mg, with doses of, e.g., about 0.25 mg, 0.5 mg, 0.75 mg, 1 mg, 1.25 mg, 1.5 mg, 1.75 mg, 2.0 mg, 2.5 mg, 3.0 mg, 3.5 mg, 4.0 mg, 4.5 mg, 5 mg, 10 mg, 15 mg, 20 mg, 25 mg, 30, mg, 35 mg, 40 mg, 45 mg, 50 mg, 75 mg, 100 mg, 125 mg, 150 mg, 175 mg, 200 mg, 225 mg, 250 mg, 275 mg, 300 mg, and 400 mg being examples.

In specific embodiments, dosages may include amounts of a hydrochloride salt or fumarate salt or freebase disclosed herein in the range of about, e.g., 1 mg to 200 mg, 1 mg to 100 mg, 1 mg to 50 mg, 1 mg to 40 mg, 1 mg to 30 mg, 1 mg to 20 mg, 1 mg to 15 mg, 0.01 mg to 10 mg, 0.1 mg to 15 mg, 0.15 mg to 12.5 mg, or 0.2 mg to 10 mg, with doses of 0.1 mg, 0.2 mg, 0.3 mg, 0.4 mg, 0.5 mg, 0.6 mg, 0.7 mg, 0.8 mg, 0.9 mg, 1.0 mg, 1.5 mg, 1.75 mg, 2 mg, 2.5 mg, 2.75 mg, 3 mg, 3.5 mg, 3.75 mg, 4 mg, 4.5 mg, 4.75 mg, 5 mg, 5.5 mg, 6 mg, 6.5 mg, 7 mg, 7.5 mg, 8 mg, 8.5 mg, 9 mg, 9.5 mg, 10 mg, 11 mg, 12 mg, 15 mg, 20 mg, 25 mg, 30 mg, 35 mg, 40 mg, 45 mg, 50 mg, 60 mg, 75 mg, 80 mg, 90 mg, 100 mg, 125 mg, 150 mg, and 200 mg being specific examples of doses.

Typically, dosages of a hydrochloride salt or fumarate salt or freebase disclosed herein are administered once, twice, three or four times daily, every other day, every three days, once weekly, twice monthly, once monthly, or 3-4 times yearly to a patient in need thereof. In embodiments, the dosage is about, e.g., 1-400 mg/day, or 1-300 mg/day, or 1-250 mg/day, or 1-200 mg/day, for example 300 mg/day, 250 mg/day, 200 mg/day, 150 mg/day, 100 mg/day, 75 mg/day, 50 mg/day, 40 mg/day, 30 mg/day, 25 mg/day, 20 mg/day, 15 mg/day, 10 mg/day, 5 mg/day, or 1 mg/day.

In embodiments, pharmaceutical compositions for parenteral administration or inhalation, e.g., a spray or mist, of a fumarate salt or hydrochloride salt or freebase disclosed herein include a concentration of about 0.005 mg/ml to about 500 mg/mL. In embodiments, the compositions include a fumarate salt or hydrochloride salt or freebase disclosed herein at a concentration of, e.g., about 0.05 mg/mL to about 50 mg/mL, about 0.05 mg/mL to about 100 mg/mL, about 0.005 mg/mL to about 500 mg/mL, about 0.1 mg/mL to about 50 mg/mL, about 0.1 mg/mL to about 10 mg/mL, about 0.05 mg/mL to about 25 mg/mL, about 0.05 mg/mL to about 10 mg/mL, about 0.05 mg/mL to about 5 mg/mL, or about 0.05 mg/mL to about 1 mg/mL.

In embodiments, the composition includes a hydrochloride salt or fumarate salt or freebase disclosed herein at a concentration of, e.g., about 0.05 mg/mL to about 15 mg/mL, about 0.5 mg/mL to about 10 mg/mL, about 0.25 mg/mL to about 5 mg/mL, about 0.5 mg/mL to about 7 mg/mL, about 1 mg/mL to about 10 mg/mL, about 5 mg/mL to about 10 mg/mL, about 5 mg/mL to about 15 mg/mL, about 5 mg/mL to 25 mg/mL, about 5 mg/mL to 50 mg/mL, or about 10 mg/mL to 100 mg/mL. In embodiments, the pharmaceutical compositions are formulated as a total volume of about, e.g., 10 mL, 20 mL, 25 mL, 50 mL, 100 mL, 200 mL, 250 mL, or 500 mL.

For example, dosages may be administered to a subject once, twice, three or four times daily, every other day, every three days, once weekly, twice monthly, once monthly, or 3-4 times yearly. In embodiments, a hydrochloride salt or fumarate salt or freebase disclosed herein is administered to a subject once in the morning, or once in the evening. In embodiments, a hydrochloride salt or fumarate salt or freebase disclosed herein is administered to a subject once in the morning, and once in the evening. In embodiments, a hydrochloride salt or fumarate salt or freebase disclosed herein is administered to a subject three times a day (e.g., at breakfast, lunch, and dinner), at a dose, e.g., of 50 mg/administration (e.g., 150 mg/day).

In embodiments, a hydrochloride salt or fumarate salt or freebase disclosed herein is administered to a subject 12.5 mg/day in one or more doses. In embodiments, a hydrochloride salt or fumarate salt or freebase disclosed herein is administered to a subject 25 mg/day in one or more doses. In embodiments, a hydrochloride salt or fumarate salt or freebase disclosed herein is administered to a subject 35 mg/day in one or more doses. In embodiments, a hydrochloride salt or fumarate salt or freebase disclosed herein is administered to a subject 50 mg/day in one or more doses. In embodiments, a hydrochloride salt or fumarate salt or freebase disclosed herein is administered to a subject 75 mg/day in one or more doses. In embodiments, a hydrochloride salt or fumarate salt or freebase disclosed herein is administered to a subject 100 mg/day in one or more doses. In embodiments, a hydrochloride salt or fumarate salt or freebase disclosed herein is administered to a subject 150 mg/day in one or more doses. In embodiments, a hydrochloride salt or fumarate salt or freebase disclosed herein is administered to a subject 200 mg/day in one or more doses. In embodiments, a hydrochloride salt or fumarate salt or freebase disclosed herein is administered to a subject 250 mg/day in one or more doses.

In embodiments, the dosage of a fumarate salt or hydrochloride salt or freebase disclosed herein is 0.0005-5 mg/kg, 0.001-1 mg/kg, 0.01-1 mg/kg or 0.1-5 mg/kg once, twice, three times or four times daily. For example, in embodiments, the dosage is 0.0005 mg/kg, 0.001 mg/kg, 0.005 mg/kg, 0.01 mg/kg, 0.025 mg/kg, 0.05 mg/kg, 0.1 mg/kg, 0.15 mg/kg, 0.2 mg/kg, 0.25 mg/kg, 0.3 mg/kg, 0.4 mg/kg, 0.5 mg/kg, 0.75 mg/kg, 1 mg/kg, 2.5 mg/kg, or 5 mg/kg, once, twice, three times or four times daily. In embodiments, a subject is administered a total daily dose of 0.01 mg to 500 mg of a fumarate salt or hydrochloride salt or freebase disclosed herein once, twice, three times, or four times daily. In embodiments, the total amount administered to a subject in a 24-hour period is, e.g., 0.01 mg, 0.025 mg, 0.05 mg, 0.075 mg, 0.1 mg, 0.125 mg, 0.15 mg, 0.175 mg, 0.2 mg, 0.25 mg, 0.3 mg, 0.4 mg, 0.5 mg, 0.75 mg, 1 mg, 1.5 mg, 2 mg, 2.5 mg, 3 mg, 4 mg, 5 mg, 7.5 mg, 10 mg, 12.5 mg, 15 mg, 17.5 mg, 20 mg, 25 mg, 30 mg, 35 mg, 40 mg, 45 mg, 50 mg, 60 mg, 75 mg, 80 mg, 90 mg, 100 mg, 125 mg, 150 mg, 175 mg, 200 mg, 250 mg, 300 mg, 400 mg, or 500 mg. In embodiments, the subject may be started at a low dose and the dosage is escalated. In embodiments, the subject may be started at a high dose and the dosage is decreased.

In embodiments, a fumarate salt or hydrochloride salt or freebase disclosed herein may be administered, e.g., via inhalation or orally, at specified intervals. For example, during treatment a patient may be administered a fumarate salt or hydrochloride salt or freebase disclosed herein at intervals of every, e.g., 1 year, 6 months, 90 days, 60 days, 30 days, 14 days, 7 days, 3 days, 24 hours, 12 hours, 8 hours, 6 hours, 5 hours, 4 hours, 3 hours, 2.5 hours, 2.25 hours, 2 hours, 1.75 hours, 1.5 hours, 1.25 hours, 1 hour, 0.75 hour, 0.5 hour, or 0.25 hour.

In embodiments, a fumarate salt or hydrochloride salt or freebase of the present disclosure is administered to a patient under the supervision of a healthcare provider.

In embodiments, a fumarate salt or hydrochloride salt or freebase of the present disclosure is administered to a patient under the supervision of a healthcare provider at a clinic specializing in the delivery of psychoactive treatments.

In embodiments, a fumarate salt or hydrochloride salt or freebase of the present disclosure is administered to a patient under the supervision of a healthcare provider at a high dose intended to induce a psychedelic experience in the subject, e.g., 10 mg, 12.5 mg, 15 mg, 17.5 mg, 20 mg, 25 mg, 30 mg, 35 mg, 40 mg, 45 mg, 50 mg, 60 mg, 70 mg, 80 mg, 90 mg, 100 mg, 125 mg, or 150 mg.

In some embodiments, the administration to a patient of a high dose under the supervision of a healthcare provider occurs periodically in order to maintain a therapeutic effect in the patient, e.g., every three days, twice weekly, once weekly, twice monthly, once monthly, thrice yearly, twice yearly, or once yearly.

In some embodiments, a fumarate salt or hydrochloride salt or freebase of the present disclosure is administered by a patient on their own at home or otherwise away from the supervision of a healthcare provider.

In some embodiments, a fumarate salt or hydrochloride salt or freebase of the present disclosure is administered by a patient on their own at home or otherwise away from the supervision of a healthcare provider at a low dose intended to be sub-perceptual or to induce threshold psychoactive effects, e.g., 0.1 mg, 0.25 mg, 0.5 mg, 0.75 mg, 1 mg, 1.5 mg, 2 mg, 2.5 mg, 3 mg, 4 mg, 5 mg, 7.5 mg, or 9 mg.

In some embodiments, the administration by a patient of a low dose on their own occurs periodically in order to maintain a therapeutic effect in the patient, e.g., daily, every other day, every three days, twice weekly, once weekly, twice monthly, or once monthly.

Suitable dosage forms for a fumarate salt or hydrochloride salt or freebase disclosed herein include, but are not limited to, oral forms, such as tablets, hard or soft gelatin capsules, powders, granules and oral solutions, syrups or suspensions, troches, as well as sublingual, buccal, intratracheal, intraocular, or intranasal forms, forms adapted to inhalation, topical forms, transdermal forms, or parenteral forms, for example, forms adapted for intravenous, intra-arterial, intraperitoneal, intrathecal, intraventricular, intramuscular or subcutaneous administration. In embodiments, for such parenteral administration, it may be in the form of a sterile aqueous solution which may contain other substances, for example, enough salts or glucose to make the solution isotonic with blood. The aqueous solutions should be suitably buffered (preferably to a pH of from 3 to 9), if necessary. The preparation of suitable parenteral formulations under sterile conditions is readily accomplished by standard pharmaceutical techniques well-known to those skilled in the art.

Pharmaceutical compositions herein may be provided with immediate release, delayed release, extended release, or modified release profiles. In embodiments, pharmaceutical compositions with different drug release profiles may be combined to create a two-phase or three-phase release profile. For example, pharmaceutical compositions may be provided with an immediate release and an extended release profile. In embodiments, pharmaceutical compositions may be provided with an extended release and delayed release profile. Such compositions may be provided as pulsatile formulations, multilayer tablets, or capsules containing tablets, beads, granules, and the like. Compositions may be prepared using a pharmaceutically acceptable "carrier" composed of materials that are considered safe and effective. The "carrier" includes all components present in the pharmaceutical formulation other than the active ingredient or ingredients. The term "carrier" includes, but is not limited to, diluents, binders, lubricants, glidants, disintegrants, fillers, and coating compositions.

Pharmaceutical compositions include those suitable for oral, rectal, nasal, topical (including transdermal, buccal and sublingual), vaginal or parenteral (including subcutaneous, intramuscular, intravenous and intradermal) administration or administration via an implant. The compositions may be prepared by any method well known in the art of pharmacy.

Such methods include the step of bringing in association a fumarate salt or hydrochloride salt or freebase disclosed herein, or combinations thereof, with any auxiliary agent. The auxiliary agent(s), also named accessory ingredient(s), include those conventional in the art, such as carriers, fillers, binders, diluents, disintegrants, lubricants, colorants, flavoring agents, anti-oxidants, and wetting agents. Such auxiliary agents are suitably selected with respect to the intended form and route of administration and as consistent with conventional pharmaceutical practices.

Pharmaceutical compositions suitable for oral administration may be presented as discrete dosage units such as pills, tablets, dragées or capsules, or as a powder or granules, or as a solution or suspension. The active ingredient comprising a hydrochloride salt or fumarate salt may also be presented as a bolus or paste. The compositions can further be processed into a suppository or enema for rectal administration.

Tablets may contain the active ingredient, i.e., a fumarate salt or hydrochloride salt or freebase disclosed herein, and suitable binders, lubricants, disintegrating agents, coloring agents, flavoring agents, flow-inducing agents, and melting agents. Gelatin capsules may contain the active ingredient, i.e., a fumarate salt or hydrochloride salt or freebase disclosed herein, and powdered carriers, such as lactose, starch, cellulose derivatives, magnesium stearate, stearic acid, and the like. Similar diluents can be used to make compressed tablets. Compressed tablets can be sugar coated or film coated to mask any unpleasant taste and protect the tablet from the atmosphere, or enteric coated for selective disintegration in the gastrointestinal tract. For instance, for oral administration in the dosage unit form of a tablet or capsule, the active drug component can be combined with an oral, non-toxic, pharmaceutically acceptable, inert carrier such as lactose, gelatin, agar, starch, sucrose, glucose, methyl cellulose, magnesium stearate, dicalcium phosphate, calcium sulfate, mannitol, sorbitol and the like. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

For oral administration in liquid dosage form, the oral drug components are combined with any oral, non-toxic, pharmaceutically acceptable inert carrier such as ethanol, glycerol, water, and the like. Examples of liquid dosage forms include, but are not limited to, solutions or suspensions in water, pharmaceutically acceptable fats and oils, alcohols or other organic solvents, including esters, emulsions, syrups or elixirs, suspensions, solutions and/or suspensions reconstituted from non-effervescent granules and effervescent preparations reconstituted from effervescent granules. Such liquid dosage forms may contain, for example, suitable solvents, preservatives, emulsifying agents, suspending agents, diluents, sweeteners, thickeners, and melting agents. Liquid dosage forms for oral administration can contain coloring and flavoring to increase patient acceptance.

For parenteral administration, suitable compositions include aqueous and non-aqueous sterile solutions. In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water-soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol. The compositions may be presented in unit-dose or multi-dose containers, for example sealed vials and ampoules, and may be stored in a freeze-dried (lyophilized) condition requiring only the addition of sterile liquid carrier, for example water, prior to use. For transdermal administration, e.g. gels, patches or sprays can be contemplated. Compositions or formulations suitable for pulmonary administration, e.g. by nasal inhalation, include fine dusts or mists which may be generated by means of metered dose pressurized aerosols, nebulizers or insufflators. Parenteral and intravenous forms may also include minerals and other materials to make them compatible with the type of injection or delivery system chosen.

The fumarate salt or hydrochloride salt or freebase used in the method of the present disclosure may also be administered in the form of liposome delivery systems, such as small unilamellar vesicles, large unilamellar vesicles, and multilamellar vesicles. Liposomes can be formed from a variety of phospholipids, such as cholesterol, stearylamine, or phosphatidylcholines. The fumarate salt or hydrochloride salt or freebase may be administered as components of tissue-targeted emulsions.

The fumarate salt or hydrochloride salt or freebase used in the method of the present disclosure may also be coupled to soluble polymers as targetable drug carriers or as prodrugs. Such polymers include polyvinylpyrrolidone, pyran copolymer, polyhydroxylpropylmethacrylamide-phenol, polyhydroxyethylasparta-midephenol, or polyethyleneoxide-polylysine substituted with palmitoyl residues. Furthermore, the fumarate salt or hydrochloride salt or freebase may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels.

Pharmaceutical compositions herein may be provided with abuse deterrent features by techniques known in the art, for example, by making a tablet that is difficult to crush or to dissolve in water.

The disclosure further includes a kit, pharmaceutical composition, as hereinbefore described, in combination with packaging material, including instructions for the use of the composition for a use as hereinbefore described.

The exact dose and regimen of administration of the composition will necessarily be dependent upon the type and magnitude of the therapeutic or nutritional effect to be achieved and may vary depending on factors such as the particular fumarate salt or hydrochloride salt or freebase, formula, route of administration, or age and condition of the individual subject to whom the composition is to be administered.

The fumarate salt or hydrochloride salt or freebase used in the method of the present disclosure may be administered in various forms, including those detailed herein. The treatment with the fumarate salt or hydrochloride salt or freebase may be a component of a combination therapy or an adjunct therapy, i.e. the subject or patient in need of the drug is treated or given another drug for the disease in conjunction with one or more of the instant fumarate salt or hydrochloride salt or freebase. This combination therapy can be sequential therapy, where the patient is treated first with one drug and then the other, or the two drugs are given simultaneously. These can be administered independently by the same route or by two or more different routes of administration depending on the dosage forms employed.

In some embodiments, the fumarate salt or hydrochloride salt or freebase disclosed herein may be administered in combination with one or more other antidepressant treatments, such as, tricyclic antidepressants, MAOIs, SSRIs, and double and triple uptake inhibitors and/or anxiolytic drugs for manufacturing a medicament for treating depression, anxiety, and/or other related diseases, including to provide relief from depression or anxiety and preventing recurrence of depression or anxiety. In some embodiments, therapeutics that may be used in combination with a fumarate salt or hydrochloride salt or freebase of the present disclosure include, but are not limited to, Anafranil, Adapin, Aventyl, Elavil, Norpramin, Pamelor, Pertofrane, Sinequan, Surmontil, Tofranil, Vivactil, Parnate, Nardil, Marplan, Celexa, Lexapro, Luvox, Paxil, Prozac, Zoloft, Wellbutrin, Effexor, Remeron, Cymbalta, Desyrel (trazodone), Savella, Fetzima, Pristiq, and Ludiomill.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

What is claimed is:

1. A crystalline salt of N-ethyl-2-(5-fluoro-1H-indol-3-yl)-N-methylethan-1-amine comprising crystalline N-ethyl-2-(5-fluoro-1H-indol-3-yl)-N-methylethan-1-amine fumarate.

2. The crystalline salt of claim 1, which is crystalline N-ethyl-2-(5-fluoro-1H-indol-3-yl)-N-methylethan-1-amine monofumarate Form 1.

3. The crystalline salt of claim 2 characterized by an X-ray powder diffraction pattern measured using Cu K-alpha radiation comprising peaks at 17.03±0.50, 17.46±0.50, 19.97±0.50, 21.47±0.50, and 23.18±0.50 degrees 2θ.

4. The crystalline salt of claim 2 characterized by an X-ray powder diffraction pattern measured using Cu K-alpha radiation comprising peaks at 17.03±0.50, 17.46±0.50, 18.30±0.50, 19.97±0.50, 21.09±0.50, 21.47±0.50, 22.22±0.50, 23.18±0.50, 23.75±0.50, and 28.67±0.50 degrees 2θ.

5. The crystalline salt of claim 2 characterized by an X-ray powder diffraction pattern measured using Cu K-alpha radiation substantially as depicted in FIG. 8.

6. The crystalline salt of claim 2 characterized by a DSC thermogram having at least one endotherm with a peak temperature of about 126° C.

7. The crystalline salt of claim 2 characterized by a DSC thermogram substantially as depicted in FIG. 10.

8. The crystalline salt of claim 1, which is crystalline N-ethyl-2-(5-fluoro-1H-indol-3-yl)-N-methylethan-1-amine monofumarate Form 2.

9. The crystalline salt of claim 8 characterized by an X-ray powder diffraction pattern measured using Cu K-alpha radiation comprising peaks at 7.09±0.50, 11.24±0.50, 21.12±0.50, 23.12±0.50, and 28.25±0.50 degrees 2θ.

10. The crystalline salt of claim 8 characterized by an X-ray powder diffraction pattern measured using Cu K-alpha radiation comprising peaks at 7.09±0.50, 11.05±0.50, 11.24±0.50, 11.80±0.50, 17.43±0.50, 21.12±0.50, 23.12±0.50, 23.73±0.50, 25.12±0.50, and 28.25±0.50 degrees 2θ.

Figure 11:
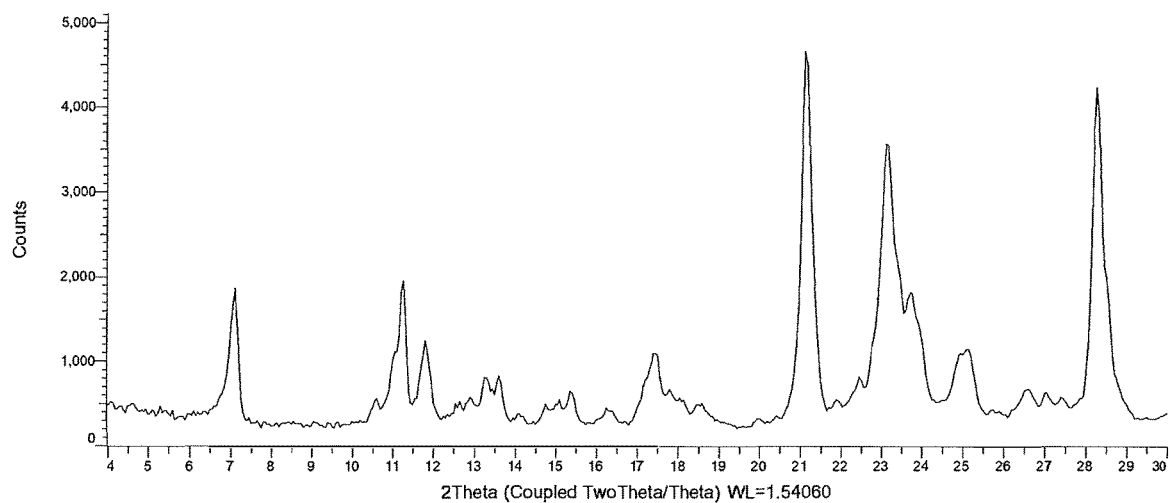
FIG. 11 depicts an XRPD diffractogram of the Form 2 polymorph of N-ethyl-2-(5-fluoro-1H-indol-3-yl)-N-methylethan-1-amine monofumarate.

11. The crystalline salt of claim 8 characterized by an X-ray powder diffraction pattern measured using Cu K-alpha radiation substantially as depicted in FIG. 11.

12. The crystalline salt of claim 8 characterized by a DSC thermogram having at least one peak temperature selected from the group consisting of about 92° C., about 101° C., and about 126° C.

13. The crystalline salt of claim 8 characterized by a DSC thermogram substantially as depicted in FIG. 13.

14. The crystalline salt of claim 1, which is crystalline N-ethyl-2-(5-fluoro-1H-indol-3-yl)-N-methylethan-1-amine hemifumarate Form 1.

15. The crystalline salt of claim 14 characterized by an X-ray powder diffraction pattern measured using Cu K-alpha radiation comprising peaks at 5.79±0.50, 11.55 0.50, 17.96±0.50, 18.49±0.50, and 22.48±0.50 degrees 2θ.

16. The crystalline salt of claim 14 characterized by an X-ray powder diffraction pattern measured using Cu K-alpha radiation comprising peaks at 5.79±0.50, 11.55±0.50, 16.28±0.50, 17.35±0.50, 17.96±0.50, 18.49±0.50, 19.23±0.50, 21.58±0.50, 22.48±0.50, and 23.59±0.50 degrees 2θ.

Figure 14:
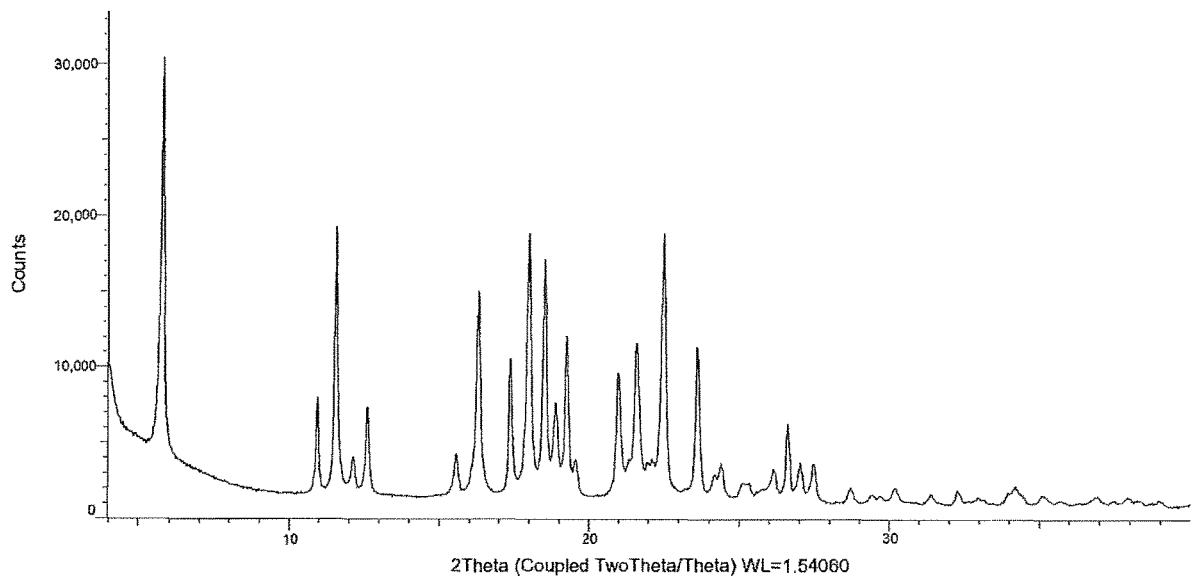
FIG. 14 depicts an XRPD diffractogram of the Form 1 polymorph of N-ethyl-2-(5-fluoro-1H-indol-3-yl)-N-methylethan-1-amine hemifumarate.

17. The crystalline salt of claim 14 characterized by an X-ray powder diffraction pattern measured using Cu K-alpha radiation substantially as depicted in FIG. 14.

18. The crystalline salt of claim 14 characterized by a DSC thermogram having at least one peak temperature selected from the group consisting of about 152° C., about 154° C., and about 161° C.

19. The crystalline salt of claim 14 characterized by a DSC thermogram substantially as depicted in FIG. 16.

20. The crystalline salt of claim 1, which is crystalline N-ethyl-2-(5-fluoro-1H-indol-3-yl)-N-methylethan-1-amine hemifumarate Form 2.

21. The crystalline salt of claim 20 characterized by an X-ray powder diffraction pattern measured using Cu K-alpha radiation comprising peaks at 7.54±0.50, 17.04±0.50, 19.78±0.50, 20.46±0.50, and 23.43±0.50 degrees 2θ.

22. The crystalline salt of claim 20 characterized by an X-ray powder diffraction pattern measured using Cu K-alpha radiation comprising peaks at 7.54±0.50, 12.86±0.50, 13.05±0.50, 16.74±0.50, 17.04±0.50, 19.78±0.50, 20.27±0.50, 20.46±0.50, 21.66±0.50, and 23.43±0.50 degrees 2θ.

23. The crystalline salt of claim 20 characterized by an X-ray powder diffraction pattern measured using Cu K-alpha radiation substantially as depicted in FIG. 17.

24. A mixture comprising at least two of the following crystalline salts: crystalline N-ethyl-2-(5-fluoro-1H-indol-3-yl)-N-methylethan-1-amine monofumarate Form 1, crystalline N-ethyl-2-(5-fluoro-1H-indol-3-yl)-N-methylethan-1-amine monofumarate Form 2, crystalline N-ethyl-2-(5-fluoro-1H-indol-3-yl)-N-methylethan-1-amine hemifumarate Form 1, and crystalline N-ethyl-2-(5-fluoro-1H-indol-3-yl)-N-methylethan-1-amine hemifumarate Form 2.

25. A solid form of N-ethyl-2-(5-fluoro-1H-indol-3-yl)-N-methylethan-1-amine comprising any one or more crystalline forms of N-ethyl-2-(5-fluoro-1H-indol-3-yl)-N-methylethan-1-amine fumarate.

26. The solid form of claim 25 comprising (a) crystalline N-ethyl-2-(5-fluoro-1H-indol-3-yl)-N-methylethan-1-amine monofumarate Form 1, crystalline N-ethyl-2-(5-fluoro-1H-indol-3-yl)-N-methylethan-1-amine monofumarate Form 2, or a mixture thereof or (b) crystalline N-ethyl-2-(5-fluoro-1H-indol-3-yl)-N-methylethan-1-amine hemifumarate Form 1, crystalline N-ethyl-2-(5-fluoro-1H-indol-3-yl)-N-methylethan-1-amine hemifumarate Form 2, or a mixture thereof.

27. The solid form of claim 25 comprising at least 50% by weight of the crystalline N-ethyl-2-(5-fluoro-1H-indol-3-yl)-N-methylethan-1-amine fumarate.

28. The solid form of claim 25 comprising at least 90% by weight of the crystalline N-ethyl-2-(5-fluoro-1H-indol-3-yl)-N-methylethan-1-amine fumarate.

29. A pharmaceutical composition comprising any one or more crystalline forms of N-ethyl-2-(5-fluoro-1H-indol-3-yl)-N-methylethan-1-amine fumarate and a pharmaceutically acceptable carrier.

30. A method of treating a mood disorder in a subject in need of such treatment comprising administering to said subject a therapeutically effective amount of the composition of claim 29.

* * * * *